(12) United States Patent
Yon et al.

(10) Patent No.: US 8,172,889 B2
(45) Date of Patent: May 8, 2012

(54) METHOD OF MANUFACTURING A HEAT TRANSFER ELEMENT FOR IN VIVO COOLING WITHOUT UNDERCUTS

(75) Inventors: Steven Yon, San Diego, CA (US); Devon Sowell, Carlsbad, CA (US)

(73) Assignee: Innercoll Therapies, Inc., San Diego, CA (US)

( * ) Notice: Subject to any disclaimer, the term of this patent is extended or adjusted under 35 U.S.C. 154(b) by 1208 days.

(21) Appl. No.: 11/974,651

(22) Filed: Oct. 15, 2007

(65) Prior Publication Data

US 2008/0046045 A1    Feb. 21, 2008

Related U.S. Application Data

(60) Division of application No. 10/785,389, filed on Feb. 24, 2004, now Pat. No. 7,288,109, which is a continuation-in-part of application No. 10/117,733, filed on Apr. 4, 2002, now Pat. No. 6,702,841.

(60) Provisional application No. 60/449,816, filed on Feb. 24, 2003, provisional application No. 60/449,809, filed on Feb. 24, 2003, provisional application No. 60/451,095, filed on Feb. 28, 2003.

(51) Int. Cl.
    *A61F 7/12*    (2006.01)
(52) U.S. Cl. .......................... 607/105; 607/104; 607/106
(58) Field of Classification Search .................... 607/96, 607/104–107, 113, 114; 164/46, 132
    See application file for complete search history.

(56) References Cited

U.S. PATENT DOCUMENTS

| | | | |
|---|---|---|---|
| 2,077,453 | A | 4/1937 | Albright |
| 2,374,609 | A | 4/1945 | McCollum |
| 2,615,686 | A | 10/1952 | Davidson |
| 2,672,032 | A | 3/1954 | Towse |
| 2,913,009 | A | 11/1959 | Kuthe |
| 3,087,493 | A | 4/1963 | Schossow |
| 3,425,419 | A | 2/1969 | Dato |
| 3,504,674 | A | 4/1970 | Swenson et al. |
| 3,612,175 | A | 10/1971 | Ford et al. |
| 3,777,343 | A | 12/1973 | D'Onofrio |
| 3,826,304 | A | 7/1974 | Withers et al. |
| 3,905,416 | A * | 9/1975 | Hammer ........................ 164/132 |
| 4,038,519 | A | 7/1977 | Foucras |
| 4,072,146 | A | 2/1978 | Howes |

(Continued)

FOREIGN PATENT DOCUMENTS

WO    WO 99/48449    9/1999

(Continued)

OTHER PUBLICATIONS

Behmann, F.W., et al.; << Heat Generation Control during Artificial Hypothermia: I: Experimental Examination of the Influence of Anesthetic Depth; Pflügers Archiv, Bd. 266, S. 408-421 (1958) (German article with English translation).

(Continued)

*Primary Examiner* — Roy Gibson

(57) ABSTRACT

An intravascular heat transfer device is provided with a mixing-inducing surface formed by an easily manufacturable process. The device can have a plurality of elongated, articulated segments, each having a mixing-inducing exterior surface. A flexible joint connects adjacent elongated, articulated segments. The device may be conveniently formed, e.g., by vapor deposition or molding, and further lacks undercuts so that the same may be conveniently removed from, e.g., a two-part mold.

4 Claims, 20 Drawing Sheets

U.S. PATENT DOCUMENTS

| | | | |
|---|---|---|---|
| 4,111,209 | A | 9/1978 | Wolvek et al. |
| 4,497,890 | A | 2/1985 | Helbert |
| RE31,873 | E | 4/1985 | Howes |
| 4,762,130 | A | 8/1988 | Fogarty et al. |
| 4,781,799 | A | 11/1988 | Herbert et al. |
| 4,863,442 | A | 9/1989 | DeMello et al. |
| 4,964,409 | A | 10/1990 | Tramulis |
| 4,973,493 | A | 11/1990 | Guire |
| 4,979,959 | A | 12/1990 | Guire |
| 5,112,438 | A | 5/1992 | Bowers |
| 5,188,602 | A | 2/1993 | Nichols |
| 5,190,539 | A | 3/1993 | Fletcher et al. |
| 5,365,750 | A | 11/1994 | Greenthal |
| 5,410,808 | A | 5/1995 | Geppelt et al. |
| 5,617,854 | A | 4/1997 | Munsif |
| 5,713,848 | A | 2/1998 | Dubrul et al. |
| 5,861,021 | A | 1/1999 | Thome et al. |
| 5,873,835 | A | 2/1999 | Hastings et al. |
| 5,899,898 | A | 5/1999 | Arless et al. |
| 5,899,899 | A | 5/1999 | Arless et al. |
| 5,957,963 | A | 9/1999 | Dobak, III |
| 6,033,383 | A | 3/2000 | Ginsburg |
| 6,096,068 | A | 8/2000 | Dobak, III et al. |
| 6,113,626 | A | 9/2000 | Clifton et al. |
| 6,126,684 | A | 10/2000 | Gobin et al. |
| 6,146,814 | A | 11/2000 | Millet |
| 6,149,673 | A | 11/2000 | Ginsburg |
| 6,165,207 | A | 12/2000 | Balding et al. |
| 6,224,624 | B1 | 5/2001 | Lasheras et al. |
| 6,231,594 | B1 | 5/2001 | Dae |
| 6,254,626 | B1 | 7/2001 | Dobak et al. |
| 6,264,679 | B1 | 7/2001 | Keller et al. |
| 6,287,326 | B1 | 9/2001 | Pecor |
| 6,436,071 | B1 | 8/2002 | Schwartz |
| 6,464,716 | B1 | 10/2002 | Dobak, III et al. |
| 6,478,812 | B2 | 11/2002 | Dobak et al. |
| 6,520,933 | B1 | 2/2003 | Evans et al. |
| 2002/0007203 | A1 | 1/2002 | Gilmartin et al. |
| 2002/0016621 | A1 | 2/2002 | Werneth et al. |
| 2002/0068964 | A1 | 6/2002 | Dobak et al. |
| 2002/0072759 | A1 | 6/2002 | Fry |
| 2002/0116039 | A1 | 8/2002 | Walker et al. |
| 2002/0183815 | A1 | 12/2002 | Nest et al. |
| 2003/0014094 | A1 | 1/2003 | Hammack |
| 2003/0040782 | A1 | 2/2003 | Walker et al. |

FOREIGN PATENT DOCUMENTS

| | | |
|---|---|---|
| WO | WO 99/66970 | 12/1999 |
| WO | WO 01/08580 | 2/2001 |
| WO | WO 01/13782 | 3/2001 |
| WO | WO 01/13809 | 3/2001 |
| WO | WO 01/13837 | 3/2001 |
| WO | WO 02/36180 | 5/2002 |

OTHER PUBLICATIONS

Behmann, F.W., et al.; Intravascular Cooling, a Method to Achieve Controllable Hypothermia; Pflügers Archive, vol. 263, pp. 145-165 (1956) (German article with English translation).

Behmann, F.W.; "Regulation of heat production in experimental hypothermia of homothermal animals"; Naunyn Schmiedebergs Arch Exp Pathol Pharmakol; 228 (1-2): 126-128 (1956). (German article with English translation).

Behmann, F.W.; "Heat Generation Control during Artificial Hypothermia, an article about the economic problem of trembling stages"; Pflügers Archive, vol. 263, pp. 166-187 (1956) (German article with English translation).

Behmann, F.W; "Heat Generation Control during Artificial Hypothermia: II. Theoretical Examinations"; Pflügers Archiv, Bd. 266, S. 422-446 (1958) (German article with English translation).

De Witte, Jan L., et al.; "Tramadol Reduces the Sweating, Vasoconstriction, and Shivering Thresholds"; Anesth Analg; vol. 87; pp. 173-179 (1998).

Hederer, G., et al.; "Animal Experiment Observations Regarding Cardiac Surgery under Intravascular Hypothermia"; Labgebbecjs Arch. U. Dtsch. A. Chir., Bd. 283, S. 601-625 (1957) (German article with English translation).

Jackson, Donald, et al; "Hypothermia : IV. Study of Hypothermia Induction Time with Various Pharmacological Agents (24617)"; Proc Soc Exp Biol Med.; 100(2): 332-335 (Feb. 1959).

Mokhtarani, Masoud, et al.; Buspirone and Meperidine Synergistically Reduce the Shivering Threshold; Anesth Analg; vol. 93; pp. 1233-1239 (2001).

Piper, S.N., et al.; "Nefopam and Clonidine in the Prevention of Postanaesthetic Shivering"; Anaesthesia; vol. 54; pp. 695-699 (1999).

Sharkey, A., et al., "Inhibition of Postanesthetic Shivering with Radiant Heat", 1987.

Wheelahan, Jennifer M., et al.; "Epidural Fentanyl Reduces the Shivering Threshold During Epidural Lidocaine Anesthesia"; Anesth Analg; vol. 87; pp. 587-590 (1998).

Zweifler et al, "Thermoregulatory vasoconstriction and shivering impede therapeutic hypothermia in acute ischemic stroke patients", 1996.

* cited by examiner

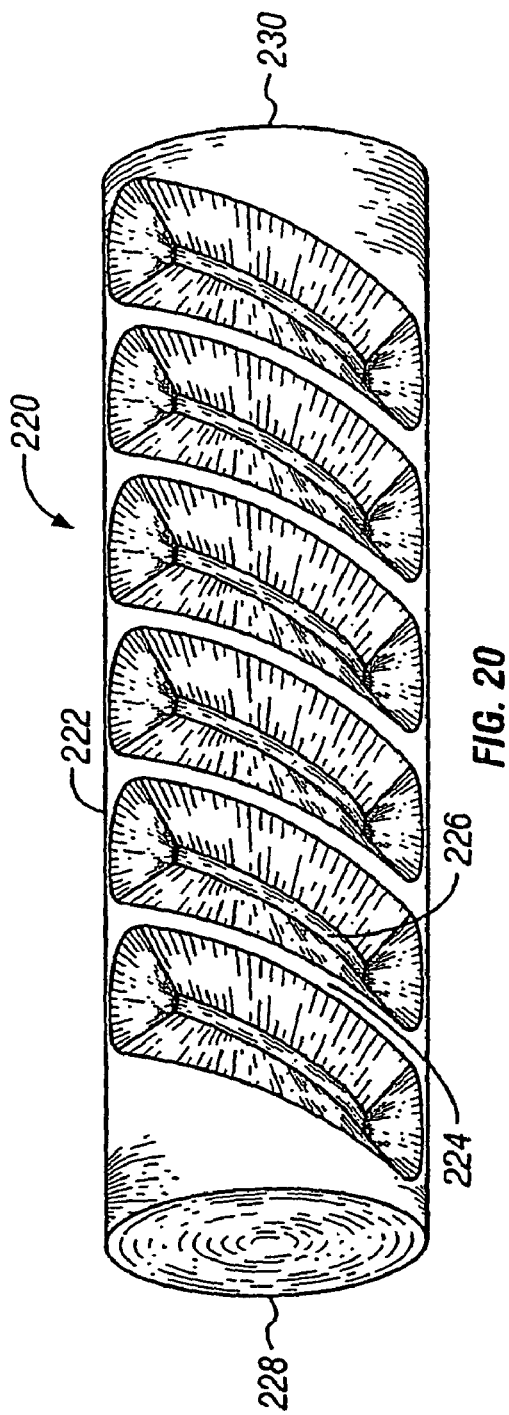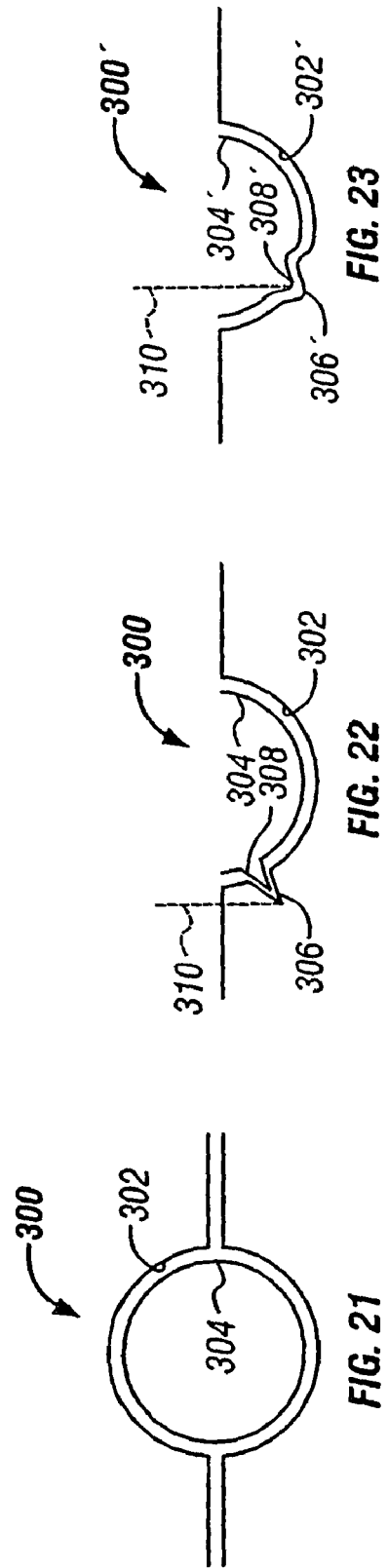
FIG. 20
FIG. 21
FIG. 22
FIG. 23

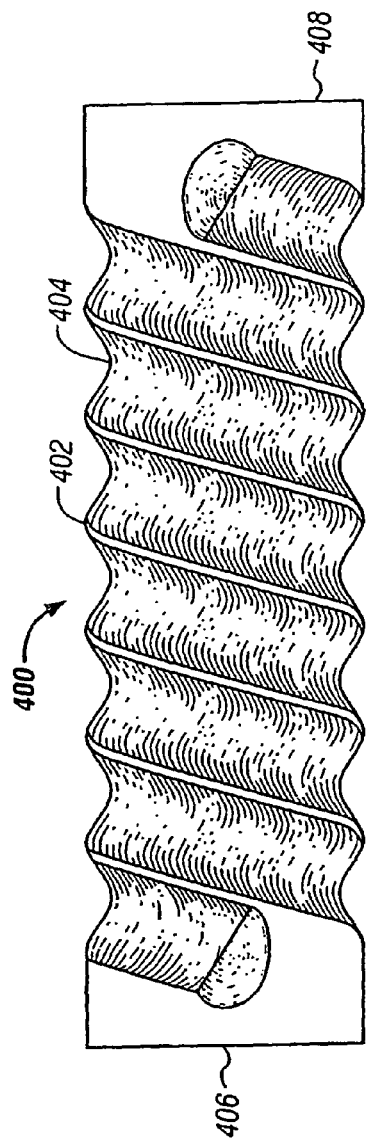
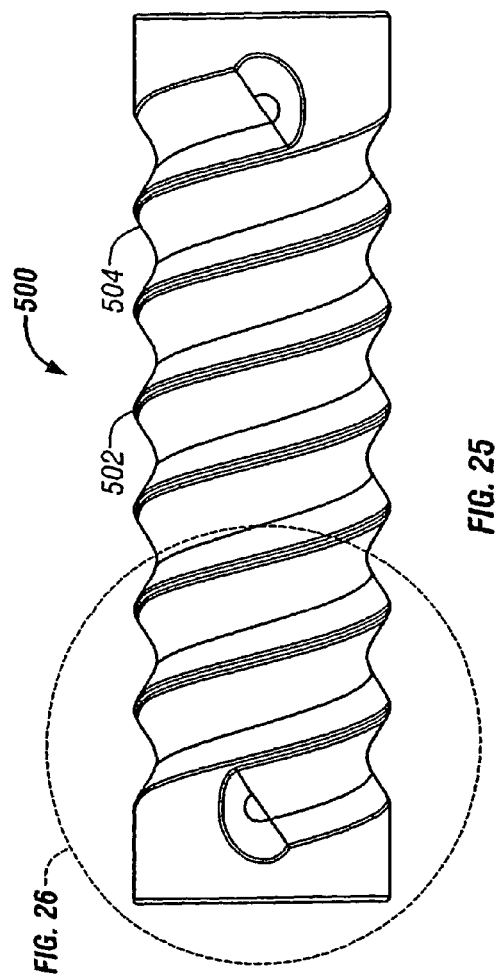

METHOD OF MANUFACTURING A HEAT TRANSFER ELEMENT FOR IN VIVO COOLING WITHOUT UNDERCUTS

CROSS REFERENCE TO RELATED APPLICATIONS

This application is a divisional of U.S. patent application Ser. No. 10/785,389, filed Feb. 24, 2004, entitled "Method Of Manufacturing A Heat Transfer Element For In Vivo Cooling Without Undercuts", which is a continuation-in-part of U.S. patent application Ser. No. 10/117,733, filed Apr. 4, 2002, entitled "Method Of Manufacturing A Heat Transfer Element For In Vivo Cooling, now U.S. Pat. No. 6,702,841.

This application also claims the benefit of U.S. provisional application Ser. Nos. 60/449,816 for a "Method of Making Heat Transfer Elements", filed Feb. 24, 2003, 60/449,809 for a "Method of Making Heat Transfer Elements", filed Feb. 24, 2003, and 60/451,095 for a "Molded Manufacture of a Heat Transfer Element", filed Feb. 28, 2003. All of the prior applications are incorporated by reference herein.

STATEMENT REGARDING FEDERALLY SPONSORED RESEARCH OR DEVELOPMENT

Not Applicable

BACKGROUND OF THE INVENTION

1. Field of the Invention

The present invention relates generally to a method for manufacturing a heat transfer element that is capable of modification and control of the temperature of a body or of a selected body organ. More particularly, the invention relates to a method for manufacturing an intravascular apparatus including a heat transfer element for controlling body and organ temperature. The invention is also directed to the resulting heat transfer element.

2. Background Information

Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Catheters have been developed which are inserted into the bloodstream of the patient in order to induce total body hypothermia. For example, U.S. Pat. No. 3,425,419 to Dato describes a method and apparatus of lowering and raising the temperature of the human body. Dato induces moderate hypothermia in a patient using a metallic catheter. The metallic catheter has an inner passageway through which a fluid, such as water, can be circulated. The Dato catheter has an elongated cylindrical shape and is constructed from stainless steel. For example, Dato suggests the use of a catheter approximately 70 cm in length and approximately 6 mm in diameter. It is clear that the Dato device has numerous limitations. For example, such a catheter would likely be inflexible and unable to navigate a tortuous vasculature.

Cooling helmets or head gear have also been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. From a practical standpoint, such devices are cumbersome and may make continued treatment of the patient difficult or impossible.

Selected organ hypothermia has been accomplished using extracorporeal perfusion, as detailed by Arthur E. Schwartz, M. D. et al., in *Isolated Cerebral Hypothermia by Single Carotid Artery Perfusion of Extracorporeally Cooled Blood in Baboons*, NEUROSURGERY, vol. 39, no. 3, p. 577 (September, 1996). However, external circulation of blood is not a practical approach for treating humans because the risk of infection, need for anticoagulation, and risk of bleeding is too great.

In all of the above, the devices have tended to have inelegant constructions, which have neglected some of the subtleties of hemocompatibility and flexibility. Therefore, a practical method to manufacture an apparatus, which is capable of modifying and controlling the temperature of a selected organ, satisfies a long-felt need.

BRIEF SUMMARY OF THE INVENTION

In one aspect, the invention is directed towards a heat transfer device for intravascular temperature control of a patient. The device includes a flexible layer of a substantially conductive material, the flexible layer having a feature to produce mixing in fluid flowing adjacent the layer, the flexible layer and feature shaped and configured such that the flexible layer may be removed from a multi-part mold in the absence of an undercut.

Implementations of the invention may include one or more of the following. The fluid may be blood, a working fluid, or both. The flexible layer may be formed of a metal such as Fe, Ti, Ta, nitinol, stainless steel, Al, Ag, Au, Cu, and Ni, or combinations thereof. The total outside diameter of the device may be between about 6 f to 18 f, and more particularly between about 9 f to 14 f. The heat transfer device may include heat transfer segments separated by articulating joints. The articulating joints may be shaped and configured as bellows or as flexible tubes. The flexible layer may have a thermal conductivity in the range of about 0.1 to 4 W/cm-K. Each segment may have at least one feature thereon, the feature including at least two helical ridges or grooves, one of the at least two helical ridges or grooves having opposite helicity from another of the helical ridges or grooves.

In another aspect, the invention is directed towards a method of making a heat transfer device. The method includes providing a mold in a deposition apparatus, the mold having an inside shape such that a flexible continuous substantially conductive layer may be deposited in the mold and shaped, configured, and arranged to have a feature that causes mixing in a fluid flowing adjacent the layer.

Implementations of the invention may include one or more of the following. The providing step may further include the step of providing a mold that is shaped, configured, and arranged to form a layer that lacks undercuts. The feature may include varieties of the feature disclosed above. The depositing may be performed by a technique selected from the group consisting of CVD, PVD, sputtering, MBE, electroplating, and ECD.

In yet another aspect, the invention is directed towards a product formed by any of the above processes.

Implementations of the invention may include one or more of the following. A protective layer may be provided that is formed of a material that is not corrosive when exposed to a working fluid, the protective layer disposed on the side of the mechanical layer opposite the biocompatible layer. A top layer of a material, chosen from the group consisting essentially of heparin, similar antithrombogenic materials and lubricious materials, may be disposed on the side of the biocompatible layer opposite the mechanical layer.

The mechanical layer may be formed of a sandwich structure including at least two layers of materials. The sandwich structure may be formed of two layers of a first material separated by a layer of a second material. The thickness of all the layers together may be less than about 1 mil in thickness. The layers of the first material may each have substantially the same thickness. The first material may be selected from the group consisting essentially of Ni, Fe, Ti, steel, Al, or other similar materials, or combinations of the same, and the second material may be selected from the group consisting essentially of Ag, Au, Cu, or other similar materials, or combinations of the same. The total diameter of the device may be between about 9 french [f] to 14 f. The heat transfer device may include heat transfer segments separated by articulating joints. The segments may be shaped and configured as helices and the joints as bellows or flexible tubes. The biocompatible coating may be selected from the group consisting essentially of Au, parylene, platinum, other similar materials, and combinations thereof. The mechanical layer may have a thermal conductivity in the range of about 0.1 to 4 W/cm-K. A protective layer may be the innermost layer, the protective layer formed of a material which is non-corrosive when exposed to a working fluid. For working fluids of saline, the protective layer may be, e.g., Au.

Implementations of the method may include one or more of the following. Either or both of a layer of an antithrombogenic material or a lubricious material may be deposited on the biocompatible coating. A protective layer may be deposited on the mandrel so as to be the innermost layer of the device, the protective layer formed of a material which does not corrode when exposed to a working fluid, such as Au. The biocompatible coating may be selected from the group consisting essentially of Au, Pt, urethane, Teflon®, other noble metals, parylene, or other similar materials or combinations thereof. The mandrel may be formed of Al, and may be formed having a shape configured and arranged such that a material formed thereon is capable of causing mixing in a fluid flowing adjacent the material. The mandrel may be formed by a technique selected from the group consisting of machining, injection molding, laser machining, hydroforming, or other similar techniques. The surface of the heat transfer device may be bombarded with nitrogen to provide a degree of thrombogenicity either in combination with or instead of an antithrombogenic coating such as heparin. In all of the above, the depositing may be performed by a technique selected from the group consisting of CVD, PVD, sputtering, MBE, electroplating, electrochemical deposition [ECD], or other similar techniques or combinations of the above. A seed layer may be deposited on the mandrel, the seed layer formed of a material which is capable of bonding to the protective layer or to the mechanical layer. The depositing a mechanical layer may include depositing a sandwich structure. The depositing a sandwich structure may include depositing a layer of a first metal, depositing a layer of a second metal, and then depositing another layer of the first metal. The first metal may be Ni and the second metal may be Cu.

Advantages of the invention are many fold. A highly conductive heat transfer element may be manufactured conveniently. The heat transfer element may retain a high degree of flexibility so as to be able to navigate tortuous vasculature. The heat transfer element has an a traumatic profile and is biocompatible.

BRIEF DESCRIPTION OF THE SEVERAL VIEWS OF THE DRAWINGS

The novel features of this invention, as well as the invention itself, will be best understood from the attached drawings, taken along with the following description, in which similar reference characters refer to similar parts, and in which:

FIGS. 19 and 20 are top and side views of another embodiment of a heat transfer device, this one being especially suited for molding via vapor deposition, inverse hydroforming, or stretchable injection molding;

FIG. 21 is a schematic depiction of a two-part molding forming a substantially cylindrical heat transfer device;

FIG. 22 is a schematic depiction of a two-part molding forming a substantially cylindrical heat transfer device that has an undercut;

FIG. 23 is a schematic depiction of a two-part molding forming a substantially cylindrical heat transfer device that does not have an undercut;

FIG. 24 is schematic drawing of an embodiment of a heat transfer device having a corkscrew design; and FIGS. 25 and 26 are schematic drawings of an embodiment of a heat transfer device having an empirically determined design having no undercut.

DETAILED DESCRIPTION OF THE INVENTION

Figure 1:
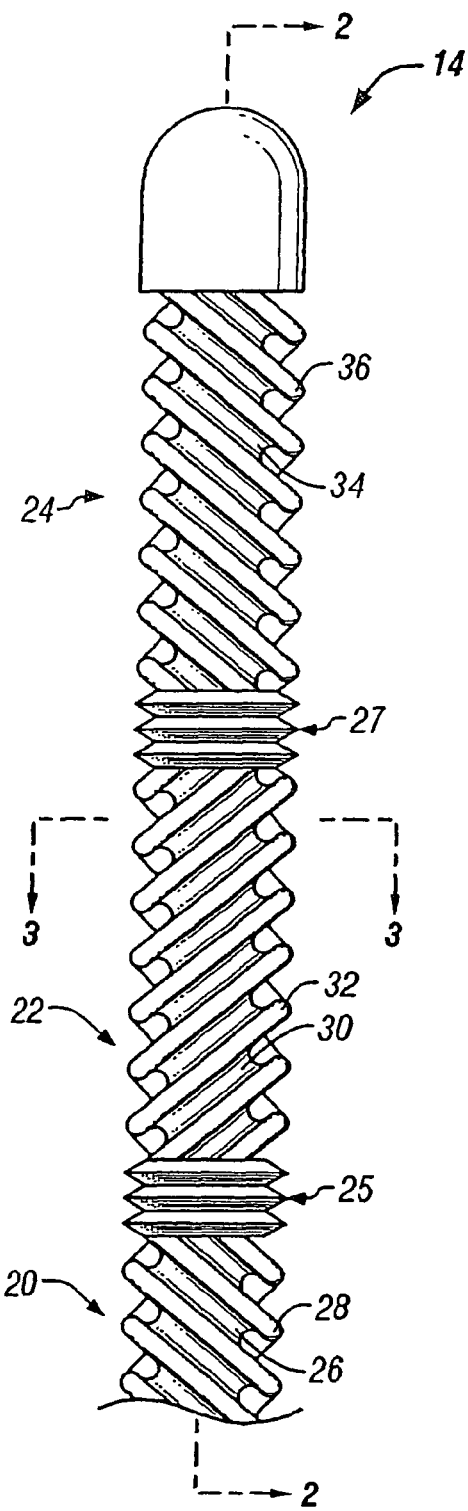
FIG. 1 is an elevation view of an embodiment of a heat transfer element according to the invention.

In order to regulate the temperature of a selected organ intravascularly, a heat transfer element may be placed in the feeding artery of the organ to absorb or deliver heat from or to the blood flowing into the organ. The transfer of heat may cause either a cooling or a heating of the selected organ. The heat transfer element must be small enough to fit within the feeding artery while still allowing a sufficient blood flow to reach the organ in order to avoid ischemic organ damage. A heat transfer element that selectively cools an organ should be capable of providing the necessary heat transfer rate to produce the desired cooling or heating effect within the organ. By placing the heat transfer element within the feeding artery of an organ, the temperature of an organ can be controlled without significantly affecting the remaining parts of the body. In contrast, by placing the heat transfer element in a large vein, such as the superior vena cava, total body cooling can be effected in a manner which avoids the deleterious consequences of prior art total body cooling.

To selectively cool the brain, for example, the heat transfer element is placed into the common carotid artery, or both the common carotid artery and the internal carotid artery. The internal diameter of the common carotid artery ranges from 6 to 8 mm and the length ranges from 80 to 120 mm. Thus, the heat transfer element residing in one of these arteries cannot be much larger than 10 f in diameter in order to avoid occluding the vessel. For placement in the superior vena cava, the size of the heat transfer element may be much larger, e.g., 14 f.

It is important that the heat transfer element be flexible in order to be placed within the small feeding artery of an organ. Feeding arteries, like the carotid artery, branch off the aorta at various levels. Subsidiary arteries continue to branch off the initial branches. For example, the internal carotid artery is a small diameter artery that branches off of the common carotid artery near the angle of the jaw. Because the heat transfer element is typically inserted into a peripheral artery, such as the femoral artery, and accesses the feeding artery by initially passing though a series of one or more of these branches, the flexibility of the heat transfer element is an important characteristic of the heat transfer element. Further, the heat transfer element is ideally constructed from a highly thermally conductive material such as metal in order to facilitate heat transfer. The use of a highly thermally conductive material increases the heat transfer rate for a given temperature differential between the coolant within the heat transfer element and the blood. This facilitates the use of a higher temperature coolant within the heat transfer element, allowing safer coolants, such as water, to be used. Highly thermally conductive materials, such as metals, tend to be rigid. Therefore, the design of the heat transfer element should facilitate flexibility in an inherently inflexible material. More details of the construction of the heat transfer element are disclosed below.

In order to obtain the benefits of hypothermia described above, it is desirable to reduce the temperature of the blood flowing to the brain (or alternatively for total body cooling, to the blood flowing out of the heart) to between 30° C. and 32° C. Given that a typical brain has a blood flow rate through each carotid artery (right and left) of approximately 250-375 cubic centimeters per minute, the heat transfer element should absorb 75-175 Watts of heat when placed in one of the carotid arteries, in order to induce the desired cooling effect. It should be noted that smaller organs may have less blood flow in the supply artery and may require less heat transfer, such as 25 Watts. For total body cooling, rates of 250-300 Watts may be required.

The magnitude of the heat transfer rate is proportional to the surface area of the heat transfer element, the temperature differential, and the heat transfer coefficient of the heat transfer element.

As noted above, the receiving vessel into which the heat transfer element is placed has a limited diameter and length. Thus, surface area of the heat transfer element must be limited, to avoid significant obstruction of the vessel, and to allow the heat transfer element to pass easily through the vascular system. For placement within the internal and common carotid artery, the cross sectional diameter of the heat transfer element is limited to about 4 mm, and its length is limited to approximately 10 cm. Other vessels may have different requirements. For example, for placement within the superior vena cava to effect total body cooling, the cross sectional diameter of the heat transfer element may be considerably larger, e.g., 12 f, 14 f, 16 f, 18 f, 20 f, or even more.

The mechanisms by which the value of the convection heat transfer coefficient may be increased are complex. However, it is known that the convection heat transfer coefficient increases with the level of turbulent kinetic energy in the fluid flow. Thus it is advantageous to have turbulent blood flow in contact with the heat transfer element. For reasons given in the parent cases of this application, turbulent flow, or at least mixing flow, can be induced using surface features on the heat transfer element. This flow can be induced both in the blood and in the working fluid. The surface features may be, as disclosed below, counter-rotating helices, non-counter-rotating helices, staggered or non-staggered protuberances, etc.

In particular, to create the desired level of mixing intensity in the blood, one embodiment of the invention uses a modular design. This design creates helical blood flow and produces a high level of mixing in the free stream by periodically forcing abrupt changes in the direction of the helical blood flow. FIG. 1 is a side view of such a mixing inducing heat transfer element which may be employed within an artery or vein. The abrupt changes in flow direction are achieved through the use of a series of two or more heat transfer segments, each comprised of one or more helical ridges.

The use of periodic abrupt changes in the helical direction of the blood flow in order to induce mixing may be illustrated with reference to a common clothes washing machine. The rotor of a washing machine spins initially in one direction causing laminar flow. When the rotor abruptly reverses direction, significant kinetic energy is created within the wash basin as the changing currents cause random mixing motion within the clothes-water slurry.

Referring to FIG. 1, the heat transfer element 14 is comprised of a series of elongated, articulated segments or modules 20, 22, 24. Three such segments are shown in this embodiment, but two or more such segments could be used without departing from the spirit of the invention. As seen in FIG. 1, a first elongated heat transfer segment 20 is located at the proximal end of the heat transfer element 14. A mixing-inducing exterior surface of the segment 20 comprises four parallel helical ridges 28 with four parallel helical grooves 26 therebetween. One, two, three, or more parallel helical ridges 28 could also be used without departing from the spirit of the present invention. In this embodiment, the helical ridges 28 and the helical grooves 26 of the heat transfer segment 20 have a left-hand twist, referred to herein as a counter-clockwise spiral or helical rotation, as they proceed toward the distal end of the heat transfer segment 20.

The first heat transfer segment 20 is coupled to a second elongated heat transfer segment 22 by a first bellows section 25, which provides flexibility and compressibility. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second bellows section 27. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twists.

In addition, the rounded contours of the ridges 28, 32, 36 also allow the heat transfer element 14 to maintain a relatively a traumatic profile, thereby minimizing the possibility of damage to the blood vessel wall. A heat transfer element according to the present invention may be comprised of one, two, three, or more heat transfer segments.

The bellows sections 25, 27 are formed from seamless and nonporous materials, such as metal, and therefore are impermeable to gas, which can be particularly important, depending on the type of working fluid which is cycled through the heat transfer element 14. The structure of the bellows sections 25, 27 allows them to bend, extend and compress, which increases the flexibility of the heat transfer element 14 so that it is more readily able to navigate through blood vessels. The bellows sections 25, 27 also provide for axial compression of the heat transfer element 14, which can limit the trauma when the distal end of the heat transfer element 14 abuts a blood vessel wall. The bellows sections 25, 27 are also able to tolerate cryogenic temperatures without a loss of performance. The bellows sections may be replaced with flexible tubes or thin-walled metal or polymers. In an alternative embodiment, the bellows may be replaced by helical springs which are then coated with a polymer to make a fluid-tight seal. As it is believed that the majority of the heat transfer is through the heat transfer segments, as opposed to the bellows, such an embodiment would be unlikely to unduly affect the heat transfer.

Figures 2, 3:
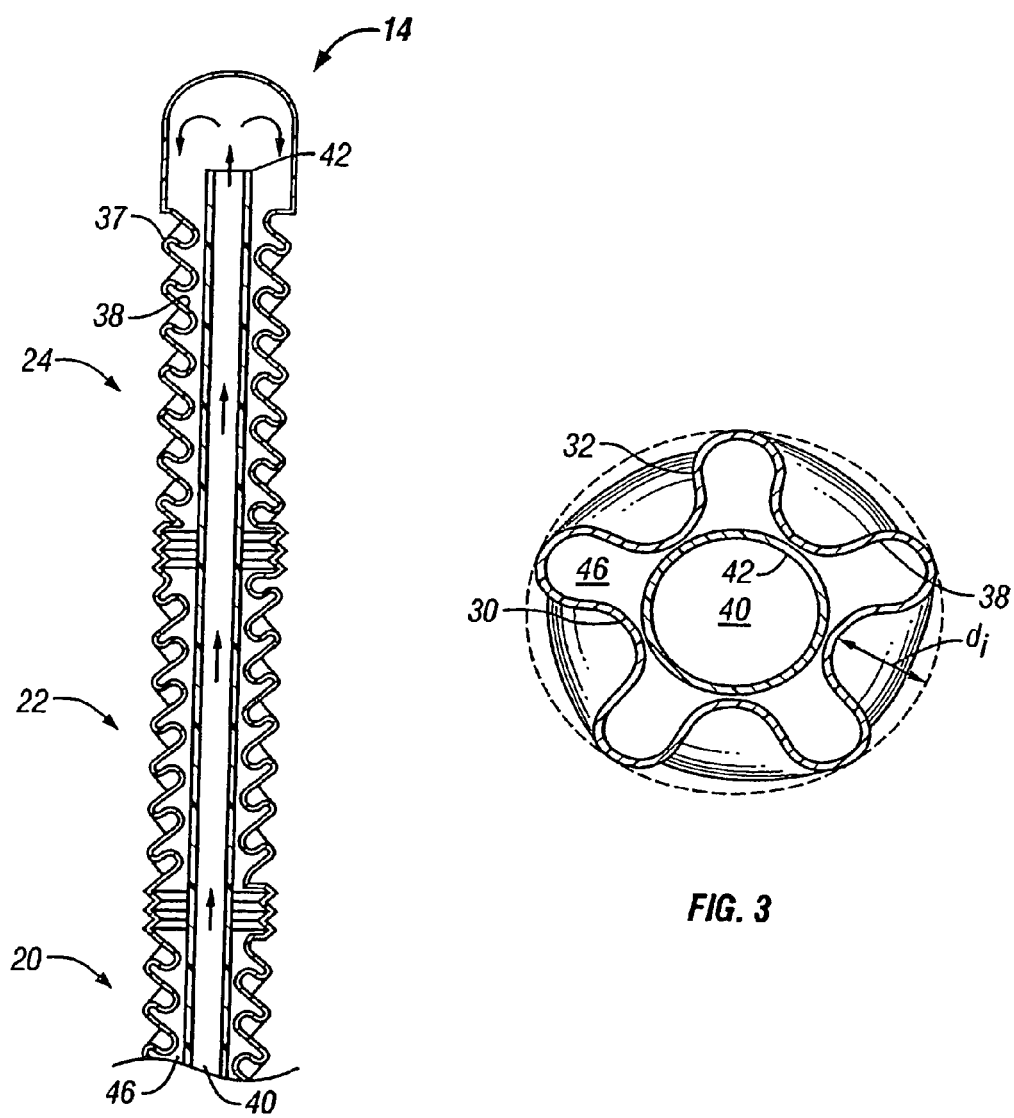
FIG. 2 is longitudinal section view of the heat transfer element of FIG. 1.
FIG. 3 is a transverse section view of the heat transfer element of FIG. 1.

FIG. 2 is a longitudinal sectional view of the heat transfer element 14 of an embodiment of the invention, taken along line 2-2 in FIG. 1. Some interior contours are omitted for purposes of clarity. An inner tube 42 creates an inner coaxial lumen 40 and an outer coaxial lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner coaxial lumen 40. At the distal end of the heat transfer element 14, the working fluid exits the inner coaxial lumen 40 and enters the outer lumen 46. As the working fluid flows through the outer lumen 46, heat is transferred from the working fluid to the exterior surface 37 of the heat transfer element 14. Because the heat transfer element 14 is constructed from a high conductivity material as explained in more detail below, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or another similar polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid which remains a liquid as the coolant. Other coolants, such as freon, undergo nucleate boiling and create mixing through a different mechanism. Saline is a safe coolant because it is non-toxic, and leakage of saline does not result in a gas embolism, which could occur with the use of boiling refrigerants. Since mixing in the coolant is enhanced by the shape of the interior surface 38 of the heat transfer element 14, the coolant can be delivered to the heat transfer element 14 at a warmer temperature and still achieve the necessary heat transfer rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element 14 stiff and cause it to push against the wall of the blood vessel, thereby shielding part of the exterior surface 37 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

FIG. 3 is a transverse sectional view of the heat transfer element 14 according to an embodiment of the invention, taken at a location denoted by the line 3-3 in FIG. 1. FIG. 3 illustrates a five-lobed embodiment, whereas FIG. 1 illustrates a four-lobed embodiment. As mentioned earlier, any number of lobes might be used. In FIG. 3, the coaxial construction of the heat transfer element 14 is clearly shown. The inner coaxial lumen 40 is defined by the insulating coaxial tube 42. The outer lumen 46 is defined by the exterior surface of the insulating coaxial tube 42 and the interior surface 38 of the heat transfer element 14. In addition, the helical ridges 32 and helical grooves 30 may be seen in FIG. 3.

As noted above, in the preferred embodiment, the depth of the grooves, $d_i$, may be greater than the boundary layer thickness which would have developed if a cylindrical heat transfer element were introduced. For example, in a heat transfer element 14 with a 4 mm outer diameter, the depth of the invaginations, $d_i$, may be approximately equal to 1 mm if designed for use in the carotid artery.

Although FIG. 3 shows four ridges and four grooves, the number of ridges and grooves may vary. Thus, heat transfer elements with 1, 2, 3, 4, 5, 6, 7, 8 or more ridges are specifically contemplated.

Referring back to FIG. 1, the heat transfer element 14 has been designed to address all of the design criteria discussed above. First, the heat transfer element 14 is flexible and is made of a highly conductive material. The flexibility is provided by a segmental distribution of bellows sections 25, 27 that provide an articulating mechanism. Bellows have a known convoluted design that provides flexibility. Second, the exterior surface area 37 has been increased through the use of helical ridges 28, 32, 36 and helical grooves 26, 30, 34. The ridges also allow the heat transfer element 14 to maintain a relatively a traumatic profile, thereby minimizing the possibility of damage to the vessel wall. Third, the heat transfer element 14 has been designed to promote turbulent kinetic energy both internally and externally. The modular or segmental design allows the direction of the invaginations to be reversed between segments. The alternating helical rotations create an alternating flow that results in mixing the blood in a manner analogous to the mixing action created by the rotor of a washing machine that switches directions back and forth. This mixing action is intended to promote high level turbulent kinetic energy to enhance the heat transfer rate. The alternating helical design also causes beneficial mixing, or turbulent kinetic energy, of the working fluid flowing internally.

Figure 4:
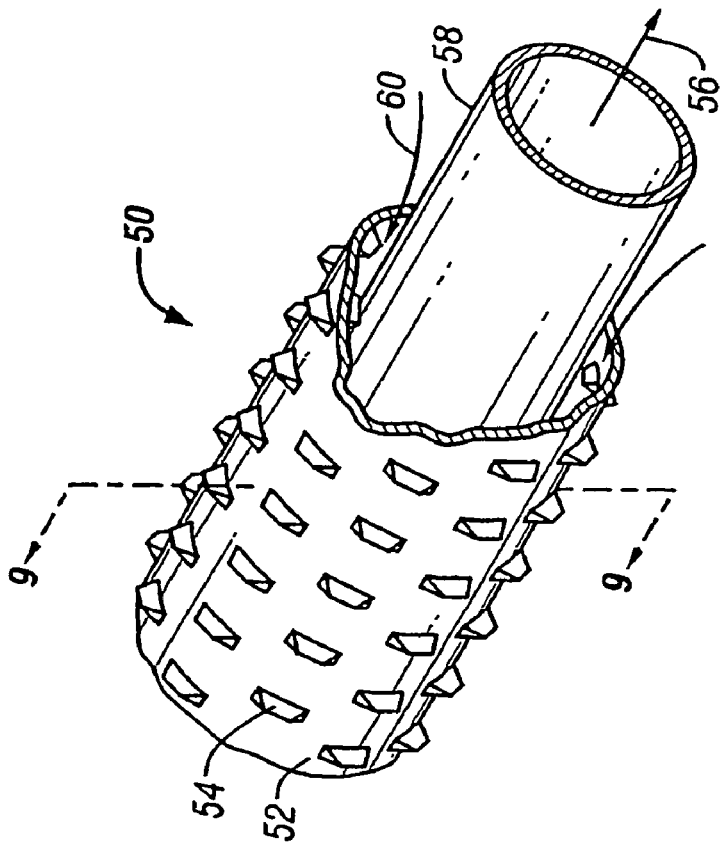
FIG. 4 is a cut-away perspective view of an alternative embodiment of a heat transfer element according to the invention.

FIG. 4 is a cut-away perspective view of an alternative embodiment of a heat transfer element 50. An external surface 52 of the heat transfer element 50 is covered with a series of axially staggered protrusions 54. The staggered nature of the outer protrusions 54 is readily seen with reference to FIG. 5 which is a transverse cross-sectional view taken at a location denoted by the line 5-5 in FIG. 4. In order to induce free stream mixing, the height, $d_p$, of the staggered outer protrusions 54 may be greater than the thickness of the boundary layer which would develop if a smooth heat transfer element had been introduced into the blood stream. As the blood flows along the external surface 52, it collides with one of the staggered protrusions 54 and a turbulent wake flow is created behind the protrusion. As the blood divides and swirls along side of the first staggered protrusion 54, its turbulent wake encounters another staggered protrusion 54 within its path preventing the re-lamination of the flow and creating yet more mixing. In this way, the velocity vectors are randomized and mixing is created not only in the boundary layer but also in at least a portion of the free stream. As is the case with the preferred embodiment, this geometry also induces a mixing effect on the internal coolant flow.

Figure 5:
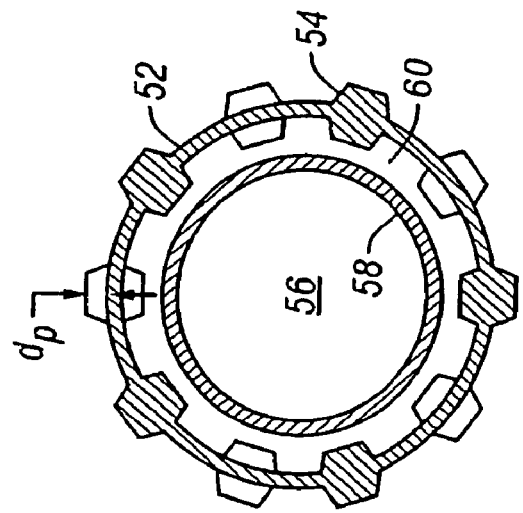
FIG. 5 is a transverse section view of the heat transfer element of FIG. 4.

In use, a working fluid is circulated up through an inner coaxial lumen 56 defined by an insulating coaxial tube 58 to a distal tip of the heat transfer element 50. The working fluid then traverses an outer coaxial lumen 60 in order to transfer heat to the exterior surface 52 of the heat transfer element 50. The inside surface of the heat transfer element 50 is similar to the exterior surface 52 in order to induce mixing flow of the working fluid. The inner protrusions can be aligned with the outer protrusions 54, as shown in FIG. 5, or they can be offset from the outer protrusions 54, as shown in FIG. 4.

The heat transfer element can absorb or provide over 75 Watts of heat to the blood stream and may absorb or provide as much as 100 Watts, 150 Watts, 170 Watts, 250 Watts, 300 Watts, or more. For example, a heat transfer element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

The method of manufacturing a heat transfer element will now be described in more detail. The exterior structure of the heat transfer element is of a complex shape as has been described in order to induce mixing in the flow of blood around the heat transfer element, as well as to induce mixing in the flow of working fluid within the heat transfer element. As may be clear, many varieties and shapes may be employed to cause such flow. Such shapes are termed herein as "mixing-inducing shapes". Examples of mixing-inducing shapes include: helical, alternating helical or other enantiomorphic shapes, aberration-including shapes, bump-including shapes, channel-including shapes, crenellated shapes, hook- or horn-shapes, labyrinthine shapes, and any other shapes capable of inducing mixing. Thus, the metallic element or elements or compounds forming the heat transfer element must be sufficiently ductile to assume such shapes during deposition.

It is further noted here that while the generic term "deposition" is used, this term is intended broadly to cover any process in which metals or coating may be disposed on a mandrel or other layer of a heat transfer element. For example, deposition may include: CVD, PVD, sputtering, MBE, forms of crystal or amorphic material "growth", spray coating, electroplating, ECD, and other methods which may be employed to form a mandrel or a coating having a mixing-inducing shape. Methods such as ECD and electroplating have the benefit of having a charged workpiece—this charge may be employed to fix the workpiece to the tool.

In general, the processes which may be employed to form the heat transfer element include forming a mandrel having a mixing inducing shape, coating the mandrel with a metal layer or a series of layers (i.e., the heat transfer element), and dissolving the mandrel.

A first step in the process of forming a heat transfer element may be to form a mandrel. One type of mandrel may be made of aluminum such as Al 6061 with a T6 heat treatment. Aluminum is useful because the same is capable of being dissolved or leached out easily with a caustic soda. A hole disposed along the axis of the heat transfer element may speed such leaching. The mandrel may be formed by machining such as by a Citizen Swiss Screw Machine. The mandrel may also be made via injection molding if the same is made of plastic, wax, low-melting-temperature thermoplastics, and the like. Other methods which may be employed to form the mandrel include machining via laser (note that laser forming is typically only employed for the outside of an element), hydroforming, and other similar methods.

Preparation of the aluminum mandrel may include some method of covering non-conductive inclusions with a conductive layer so that subsequent electrodeposits are not required to bridge the non-conducting spots. Both electrodeposited copper (which readily bridges non-conducting inclusions) and electro-less silver have been suggested for this purpose. Displacement films (typically zincate or stannate) may be used to protect the aluminum mandrel from oxidation prior to plating and improve adhesion of subsequent electrodeposits.

However the mandrel is formed, it is important for the same to have a smooth surface finish and exterior texture. In this way, the resulting heat transfer element will be smooth. A smooth mandrel allows an a traumatic device to be formed around the same. A smooth mandrel also allows a smooth metallic coating (heat transfer element) to be simply deposited around the same thus ensuring uniform heat transfer, a constant thickness of biocoating, an a traumatic profile, etc.

Figure 6:
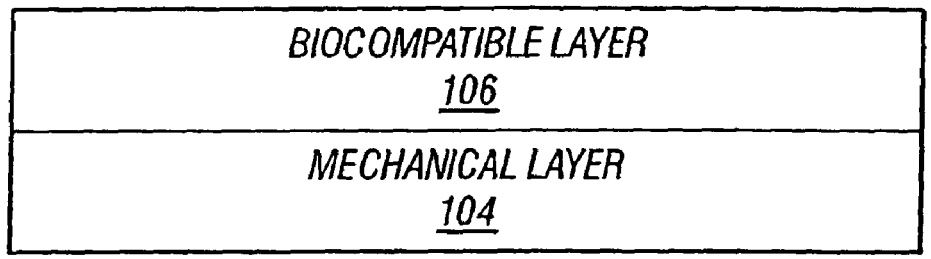
FIG. 6 is a schematic representation of layers constituting a wall of the heat transfer element according to an embodiment of the invention and formed by a method according to the invention.

A basic series of coating layers is shown in FIG. 6. FIG. 6 shows a mechanical layer 104, typically made of a metal, and a biocompatible layer 106. The mechanical layer 104 is the basic conductive element. The mechanical layer 104 is responsible for heat conduction to provide cooling and thus should have a thermal conductivity in the range of about 0.1 to 4 W/cm-K, so long as such materials can be deposited. Typical metals which may be employed for the mechanical layer 104 include Ni, Cu, Au, Ag, Ti, Ta, nitinol, stainless steel, etc. or combinations of these or other similar elements. The thickness of the mechanical layer should be less than about 2 mils thick to allow for sufficient flexibility to navigate tortous vasculature, although this is strongly dependent on the type of metal and on the tortuousity of the vasculature involved. Regarding the type of metal, any noble metal may be employed. Certain of these have deleterious biocompatibility, however, and each has different manufacturing concerns. For example, a Au heat transfer element would require a seed layer since Au will not stick to the Al mandrel.

Ni has been found to be useful. Cu is also useful and has a high conductivity; unfortunately, Cu is also likely to assume the form of the vasculature in which the same is disposed.

Some manufacturing details follow. Electroless nickel deposits containing significant phosphorus tend to be more resistant to corrosion, relative to electro-deposited nickel, in saline environments. Use of phosphorus-containing electroless nickel as a pre-plate, prior to deposition of the electroless or electrolytic structural nickel, may result in a more corrosion resistant electroform. At higher anode potentials (increased plating rate), nickel sulfamate plating solutions are subject to anodic oxidation of the sulfamate ion and incorporation of sulfur compounds into the electrodeposit, reducing ductility and increasing electrochemical reactivity. Using DC electrodeposition, varying anode potential produces electrodeposits with varying grain size and shape. Optimizing the process for the desired properties of the electrodeposit (e.g. ductility or porosity) may include an analysis of the effect of anode potential. Cobalt co-deposited with Nickel can increase the hardness and tensile strength of the electrodeposit. The porosity of the electrodeposited nickel may be mitigated by interrupting the nickel deposition with a medial layer with good leveling, such as electrodeposited copper.

The order of process steps required for production of an electroform may be optimized to prevent contact of electrodeposits with harmful solutions. For example, deposition of cyanide gold may require post-rinsing with an oxidizer (typically a hypochlorite). This rinse will attack any exposed nickel. A hypochlorite rinse should therefore be applied only to electroforms before removal of the aluminum mandrel to minimize nickel exposure.

Pulse plating has been demonstrated to reduce porosity by grain refinement and to reduce the requirement for additives. In addition, pulse plated deposits have demonstrated greater ductility than DC plated deposits.

Under axial elongation, bellows convolutions are subject to tensile stress (normal to the circumferential direction) at the inner diameter and compressive stress (normal to the circumferential direction) at the outer diameter. The elongation (prior to fracture) of flexible bellows is maximized by increasing the ductility of the material (electrodeposit) thereby allowing plastic elongation, prior to failure, of the bellows internal diameter.

For sake of argument, it is assumed here that Ni forms the basic heat transfer element. As stated above, Ni is not hemocompatible. Thus, a biocompatible layer 106 is disposed on the mechanical layer 104 as is shown in FIG. 6. The biocompatible layer may be, e.g., urethane, parylene, Teflon®, a lubricious coating, an antithrombogenic coating such as heparin, a noble metal such as Au, or combinations of the above or other similar materials.

One difficulty with the above embodiment may be that, with use of certain working fluids, such as saline, corrosion of the mechanical layer may occur. In the case of a mechanical layer 104 of Ni, saline may be especially corrosive. Thus, a protective layer 102 may be employed that is noncorrosive with respect to saline. For example, the protective layer 102 may be made of Au. A Au protective layer 102 may encounter difficulties attaching to an aluminum mandrel, and thus if necessary a layer of Cu may be deposited on the mandrel prior to deposition of the Au layer. Following the dissolution of the mandrel, the Cu layer may also be etched away. The protective layer may generally be any noble or inert metal, or may be a polymer or other protective material such as Teflon®.

Alternatively, the protective layer 102 may be vacuum deposited, such as by a vapor deposition method, following removal or dissolution of the mandrel. The resulting hole left by the dissolved mandrel allows a path for vaporized gases or liquid chemicals to flow. Thus, materials can be deposited in this fashion on the inside of the heat transfer element. The materials so deposited may be the same as those discussed above: polymers, such as non-corrosive or non-polar polymers, noble metals, and the like.

Figure 7:
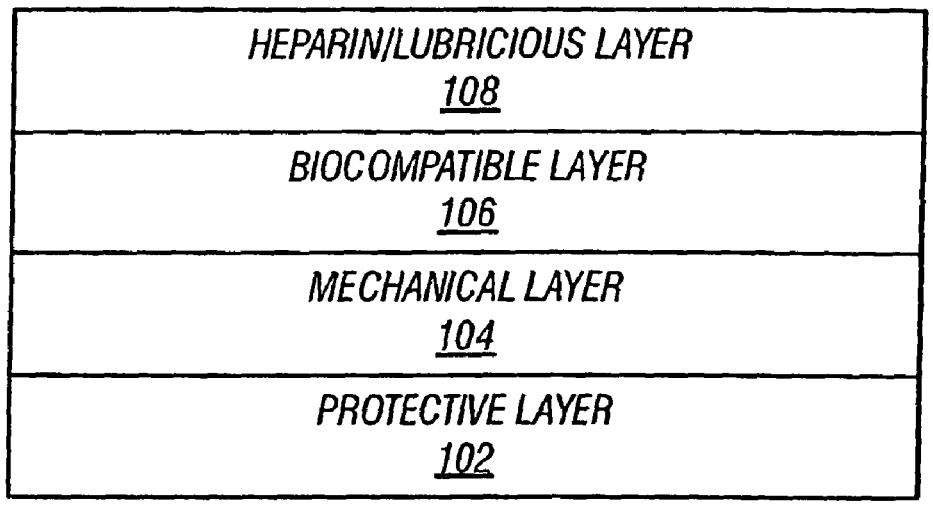
FIG. 7 is a schematic representation of layers constituting a wall of the heat transfer element according to a second embodiment of the invention and formed by a method according to the invention.

FIG. 7 also shows two layers above the mechanical layer 104: a biocompatible layer 106 and a heparin/lubricious layer 108. These may also be combined to form a single biocompatible layer. Alternatively, the biocompatible layer may be a "seed" layer which enhances the connection of the heparin/lubricious layer 108 to the underlying mechanical layer 104. Such a seed layer may be, e.g., parylene. Finally, it should be noted that the heparin/lubricious layer 108 is indicated as exemplary only: either heparin or a lubricious layer may be deposited individually or in combination. For example, in certain applications, heparin may not be necessary.

Figure 8:
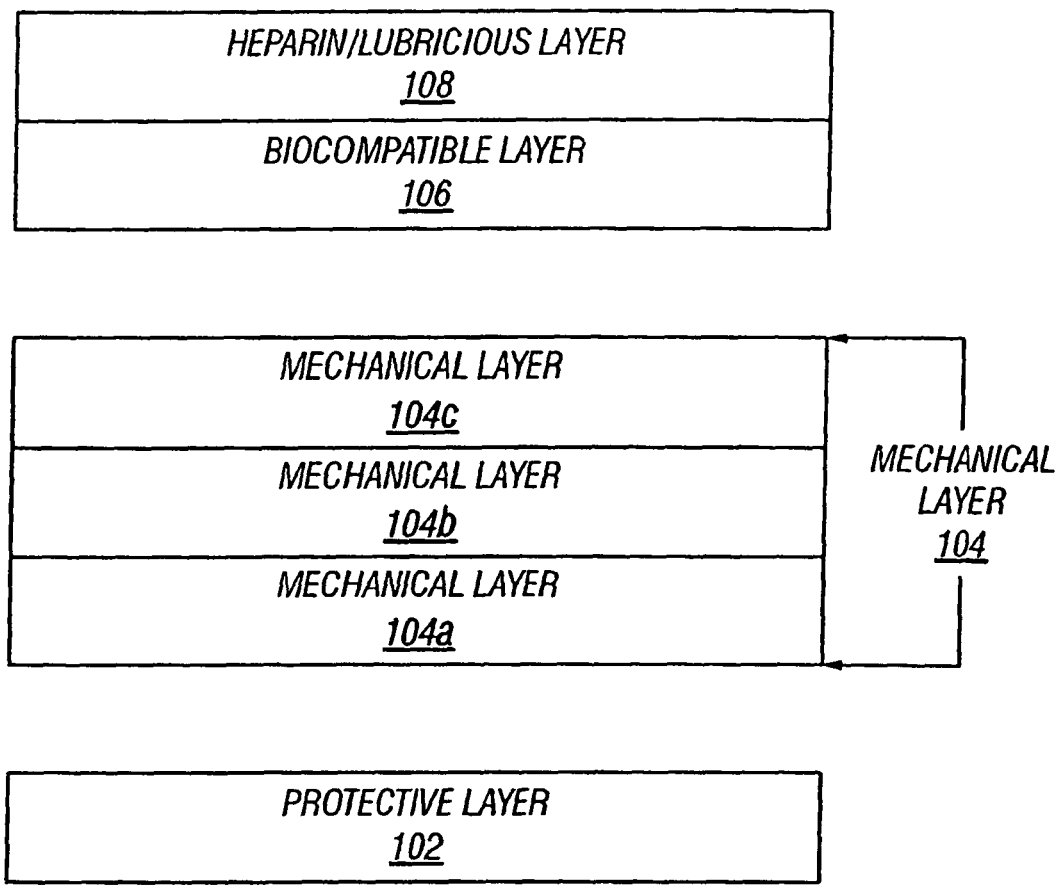
FIG. 8 is an exploded schematic representation of layers constituting a wall of the heat transfer element according to a third embodiment of the invention and formed by a method according to the invention.

Another embodiment is shown in FIG. 8. This embodiment addresses another difficulty that may occur with various metals. For example, a mechanical layer 104 that is made entirely of Ni may have too low a burst pressure, partially due to its porosity. The protective layer 102 of FIG. 7 may address some of these concerns. A better approach may be that shown in FIG. 8. In FIG. 8, the mechanical layer 104 is broken up into several layers. Two, three, or more layers may be employed. In FIG. 8, layers 104a and 104c are formed of a first material such as Ni. An interior layer 104b is deposited between layers 104a and 104c. This layer 104b may be formed of a second material such as Cu. This combination of layers 104a, 104b, and 104c forms a mechanical "sandwich" structure. The Cu layer 104b (the second "metal" or "layer") may serve to close "pinholes" that may exist within the more porous Ni layers 104a and 104c (the first "metal" or "layer").

One embodiment that has been found useful is that described by Table I below. In Table I, the biocompatible coating is a noble metal layer of Au. It should be noted that Table I describes a very specific embodiment and is provided purely for illustrative purposes. Table I should not be construed as limiting. Table I is keyed to FIG. 8.

| Layer Number | Material | Thickness |
| --- | --- | --- |
| 102 | Au (e.g., mil-g-45204, type one, grade A, class one) | 1/10 mil |
| 104a | Ni | 3½/10 to 1 mil |
| 104b | Cu | 1/10 mil |
| 104c | Ni | 3½/10 to 1 mil |
| 106 | Au | 1/10 mil |
| 108 | heparin/ lubricious | 7-10 microns |

The overall thickness of the group of layers 102-108 may be about 1 mil. The nickel and copper may contain traces of other elements without deleterious consequences.

In some cases, the heat transfer device may be constructed using a multi-part mold, and in particular a two-part mold. The difficulty in this case may often be the removal of the device from the two-part mold, especially with respect to more convoluted features, such as helical grooves, which may often get "caught" on a section of the mold and are thus rendered unremovable. This "catching" typically occurs in the context of an undercut.

For example, referring to FIG. 21, a multi-part mold 300 is schematically shown having an interior wall 302. A part 304 is shown within the mold. These shapes are to be construed generally—the part 304 and wall 302 may well have features that are convoluted, such as ridges or grooves or both, or dimples or knobs or both, etc.

Referring now to FIG. 22, a mold 300 is shown that creates an undercut in a part 304. In particular, interior wall 302 has a section 306 that creates a feature 308 in the part or heat transfer element 304. Here, "part" is intended to refer to a heat transfer element or a heat transfer segment, depending on context. In FIG. 22, the part 304 has an undercut, in particular at section 308, because the part 304 cannot be lifted up, in the direction indicated by arrow 310, without having the feature 308 "catch" on section 306. While the part may be maneuvered in such a way to remove the same from the mold, such practices are inconvenient and do not transfer well to large scale manufacturing.

Referring now to FIG. 23, a mold 300' is shown that creates a feature but not an undercut in a part 304'. In particular, an interior wall 302' of mold 300' has a section 306' that creates a feature 308' in the part or heat transfer element 304'. In FIG. 23, the part 304' does not have an undercut because the part 304' can be lifted up, in the direction indicated by arrow 310, without having the feature 308' "catch" on section 306'.

Figure 9:
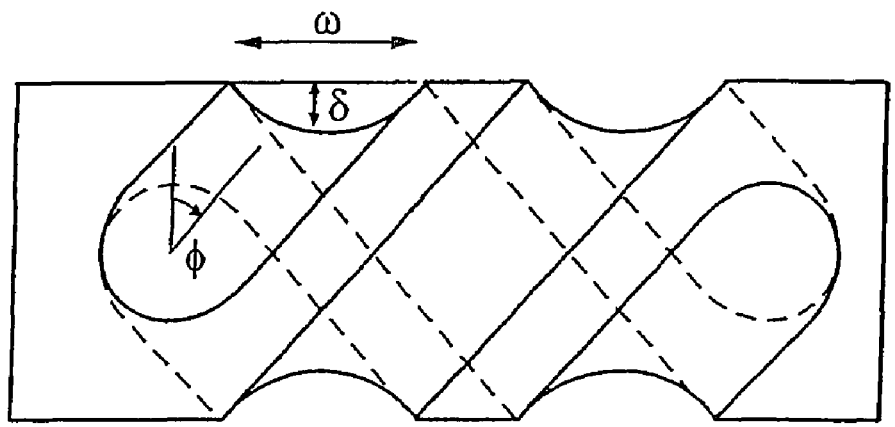
FIG. 9 is a schematic drawing of a helical groove showing variable indices for determination of optimum construction.

In an embodiment of the invention, and referring to FIG. 9, a mathematical construct is employed to find a helical groove design that can be more easily and reliably removed from a multi-part groove. Using two helical grooves with initial and terminal points at 180° intervals around the circumference of a cylinder, some combination of (φ, w, δ) should allow the resulting device to be removable from a 2-part mold. In FIG. 9, the "parting" line of the mold would be the plane of the page.

Figure 10:
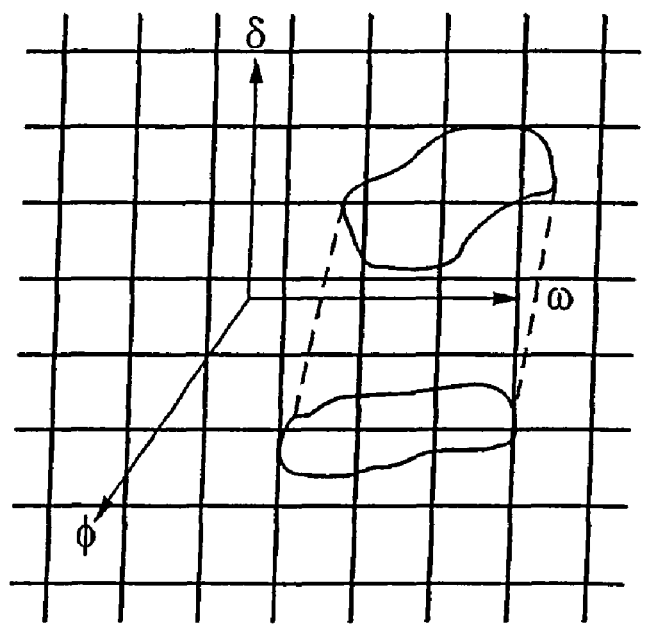
FIG. 10 is a plot of the indices of FIG. 9.

Referring to FIG. 10, an empirical exploration of the parameter space is shown. By studying this parameter space, the locus of points (φ, w, δ) should be revealed for a device that has no undercut.

As noted above, the heat transfer element employs a helical groove to impart angular momentum to the external flow, resulting in enhanced mixing and increased heat transfer relative to that which would obtain with a smoother cylindrical part. And as noted, in some embodiments, the helical groove may have pitch and depth such that its manufacture is less convenient using a 2-part mold (i.e., a mold with two halves). By relaxing the constraint on pitch (i.e. reducing pitch) and reducing the number of leads (number of distinct helices), a 2-lead helical segment with minimal undercut can be designed which may be compatible with a 2-part molding process.

If the constraint of a purely helical groove is removed, then alternate forms may be manufactured using a 2-part mold, e.g., with pitch varying along the length of the groove.

Figure 11:
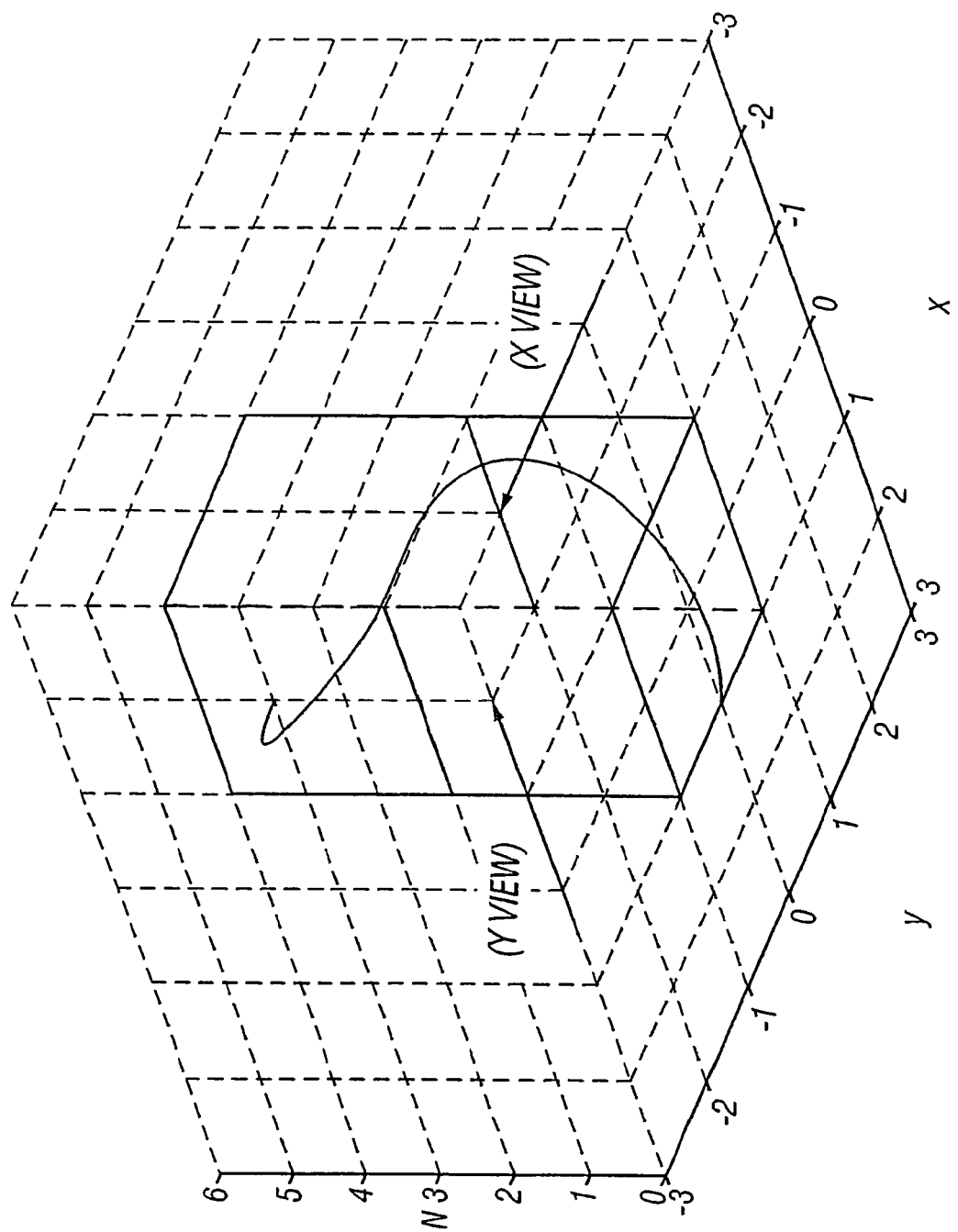
FIG. 11 is a plot showing a segment of a design for a "helical" path.
Figure 12:
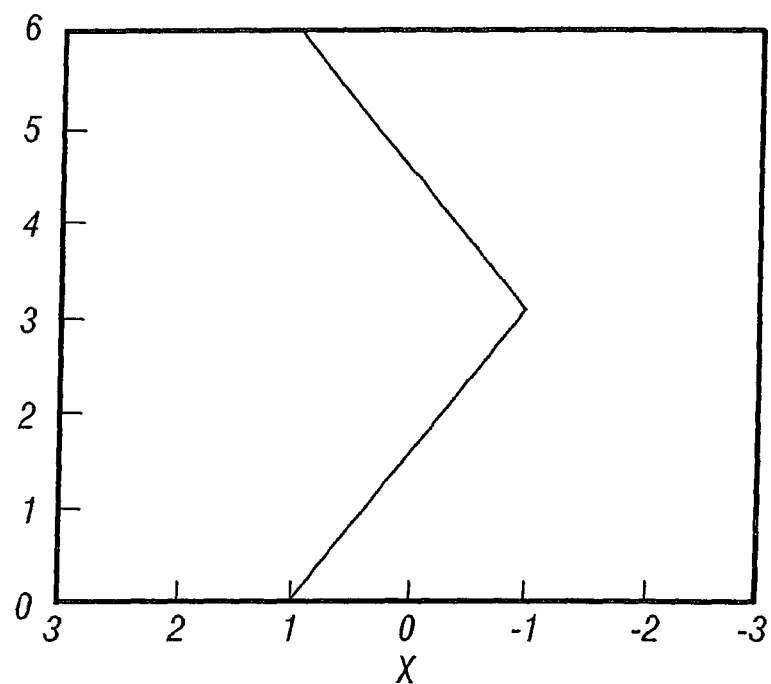
FIG. 12 is a plot of the projection along the X-view of the path of FIG. 11.
Figure 13:
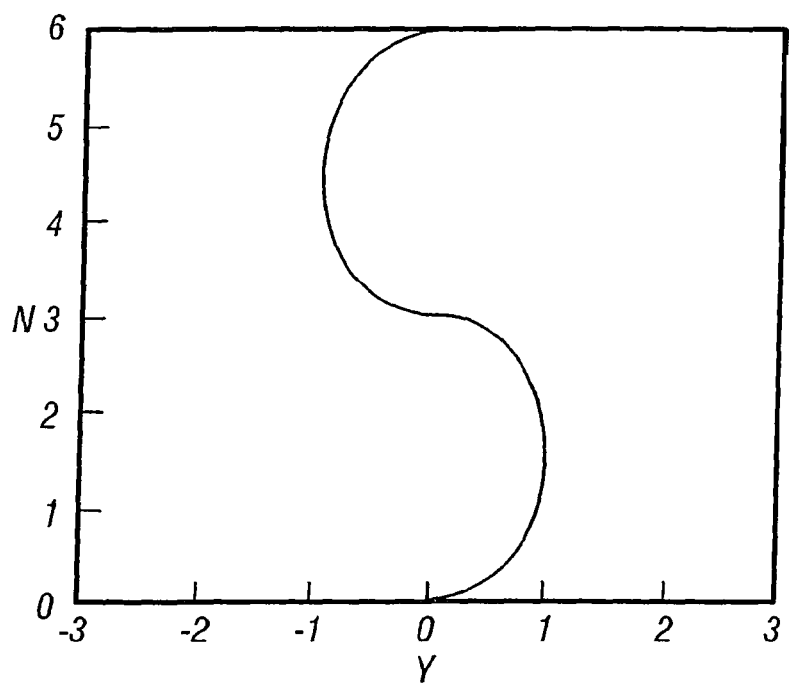
FIG. 13 is a plot of the projection along the Y-view of the path of FIG. 11.

For example, an ellipse may describe the intersection of a circular cylinder and a plane. If a sequence of similar ellipses, all circumscribed around the same right circular cylinder, are constructed such that they intersect at the termini of their major axes, then by traversing alternate halves of subsequent ellipses, a path along the length of the cylinder is obtained which contains co-planar points through each of which may be drawn a line normal to the axis of the cylinder. A short segment of the resulting (3-D) path is shown in FIG. 11. Projections of this path along the directions indicated as 'X-view' and 'Y-view' are shown in FIGS. 12 and 13, respectively. If the path shown in FIG. 11 represents the (bottom) vertex of a triangular groove machined into a larger circular cylinder, then a unique plane parallel to the plane of FIG. 12 and containing the axis of the cylinder may be defined which divides the cylinder into two halves. Since the groove is normal to the plane at the corresponding intersection (of groove and plane), each of the resulting halves may be consistent with the manufacture of the grooved cylinder using a 2-part mold. The region of the space (φ, w, δ) where φ is the angle of the major axes of the ellipses relative to the cylinder axis, and w and, δ are the width and depth, respectively, of the groove defined by path shown in FIG. 11, containing grooves which are compatible with a 2-part mold has not been determined. In any case, the relaxation of the constraint of a purely helical path allows construction of a more easily manufactured part which has on at least part of its surface a groove with sufficient pitch to enhance mixing and heat transfer.

Figure 26:
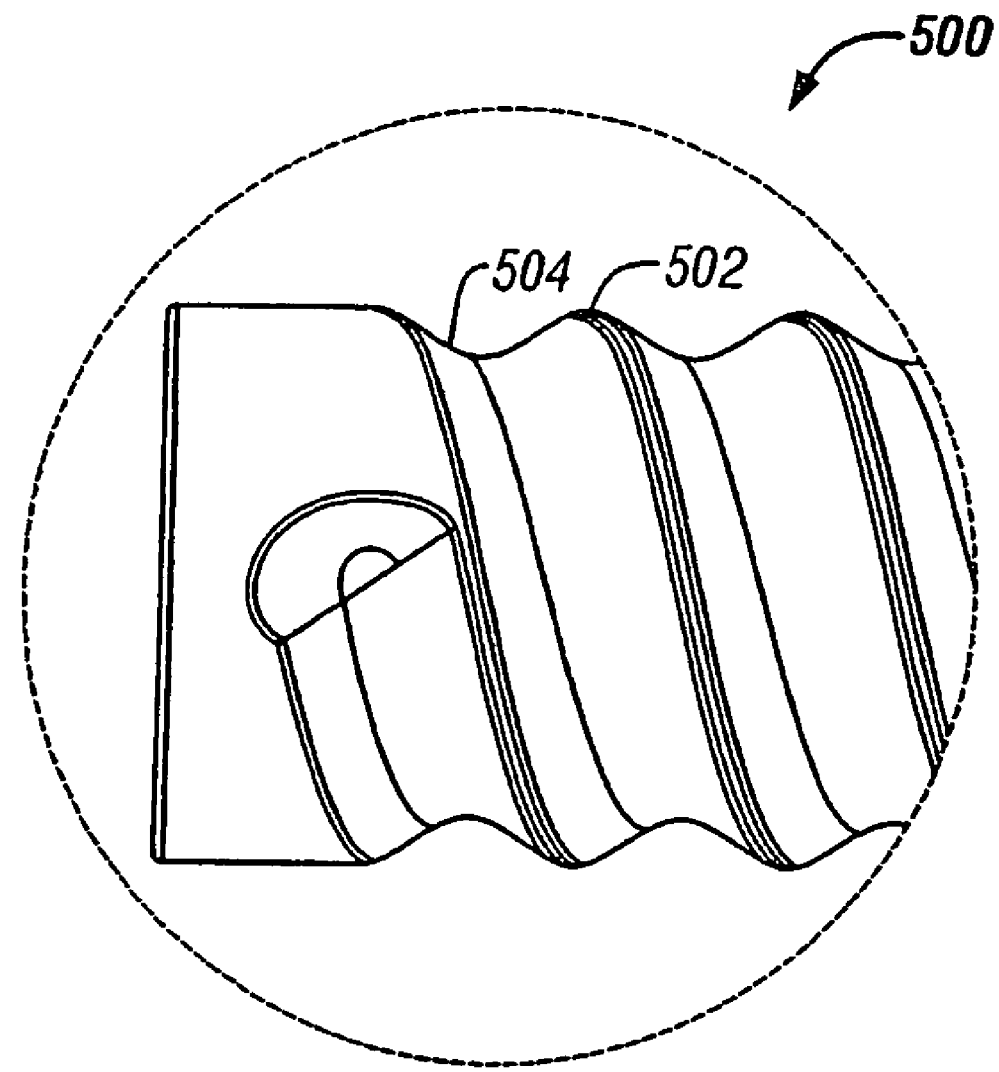

In FIG. 25, and the more detailed view thereof in FIG. 26, a part 500 is shown with ridges 502 and grooves 504 that are empirically believed to provide such heat transfer, and yet be easily removed from a mold.

Figure 14:
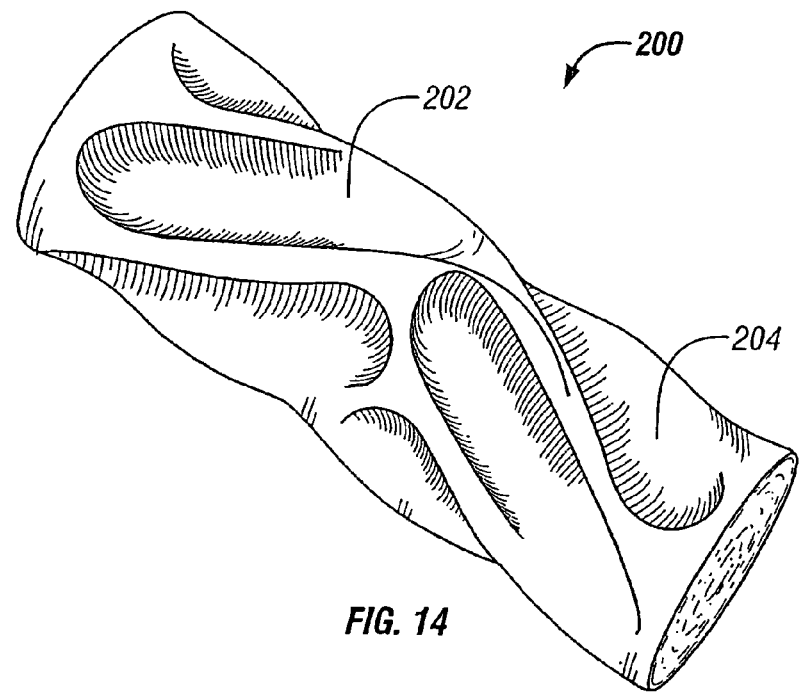
FIG. 14 is a schematic drawing of an embodiment of a heat transfer device having helical grooves of different helicities on a single segment.
Figure 15:
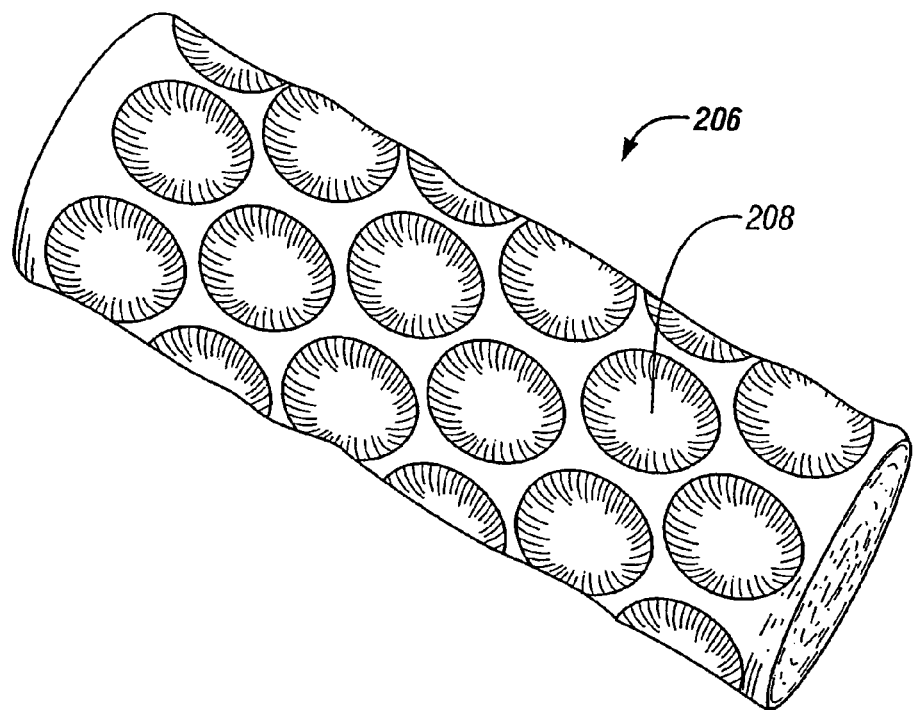
FIG. 15 is a schematic drawing of an embodiment of a heat transfer device having a dimpled design.

Other geometries may also be advantageously employed. For example, the above-mentioned embodiments generally show either all of the helical segments having either a left or right hand helical sweep per segment. Referring to FIG. 14, a design is shown that incorporates both left (202) and right (204) hand helical sweeps into one segment 200. This design may improve fluid turbulence internally as well as externally. Of course, it will be noted that pitch and the number of revolutions for these particular segments can be changed for different variations. Another possible segment for use with the heat transfer element could be a dimpled design heat transfer element 206, as shown in FIG. 15. In this embodiment, a number of dimples 208 are shown. The turbulence internally and externally may be improved in this design.

Figure 16:
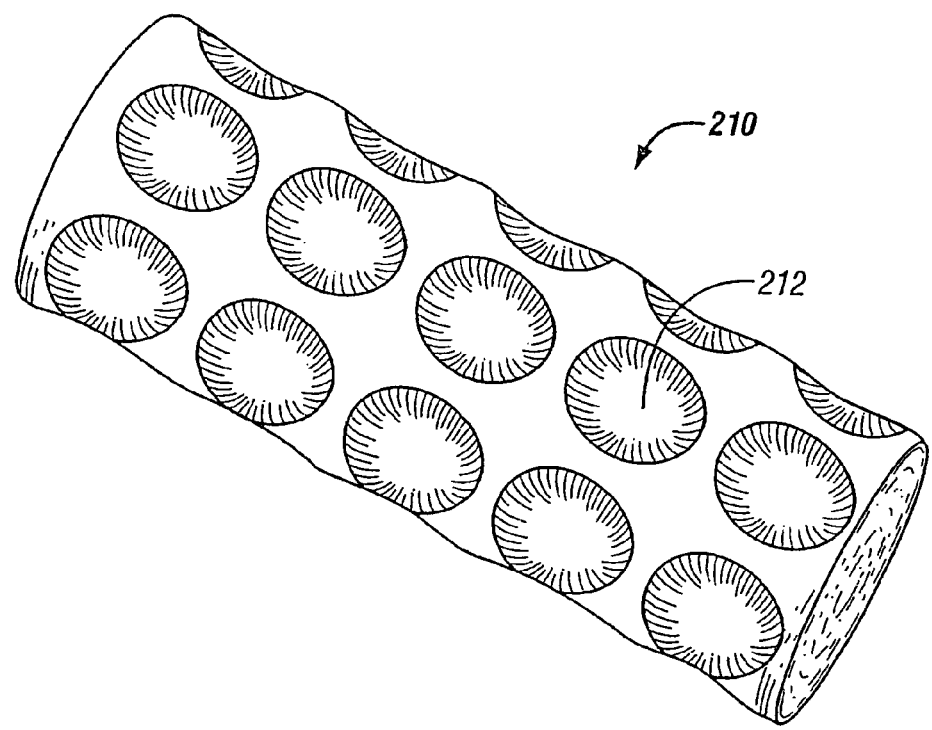
FIG. 16 is another schematic drawing of another embodiment of a heat transfer device having a dimpled design.

In a related embodiment, as shown in FIG. 16, a heat transfer segment 210 has a series of dimples 212 arranged in a straight line, parallel to the axis of the segment.

Figure 17:
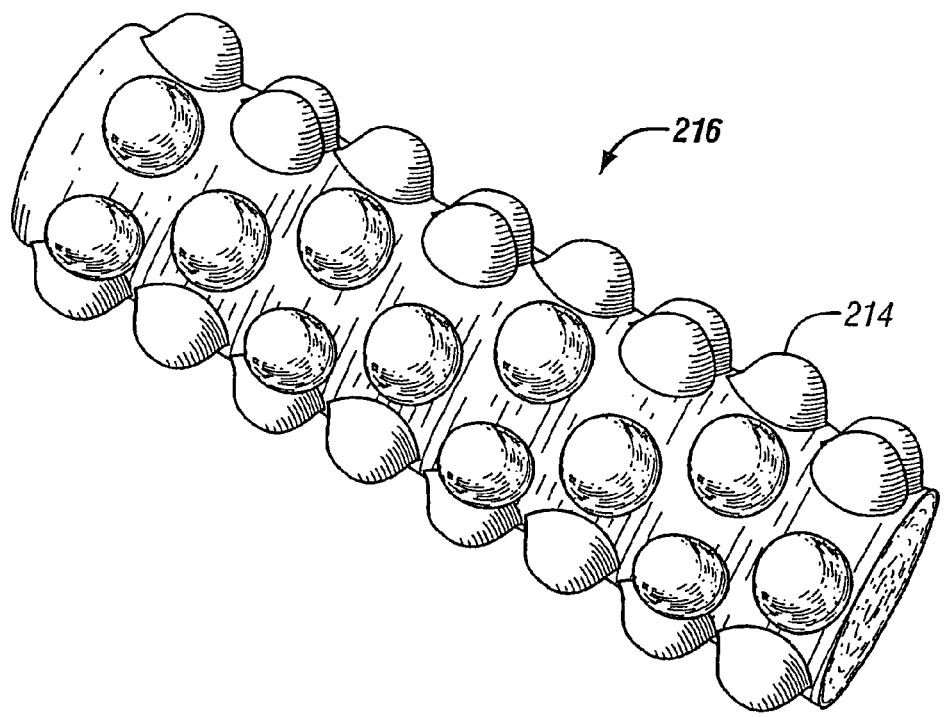
FIG. 17 is another schematic drawing of another embodiment of a heat transfer device having a dimpled design.
Figure 18:
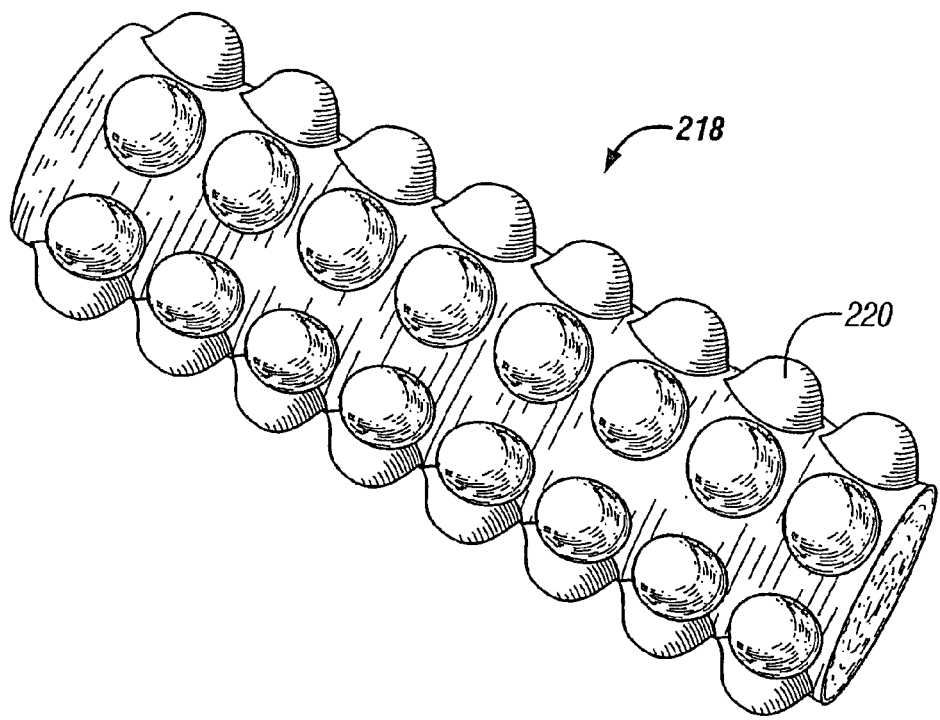
FIG. 18 is another schematic drawing of another embodiment of a heat transfer device having a dimpled design.

In another related embodiment, the dimples may be inverted to form knobs 214, as shown in the heat transfer segment 216 of FIG. 17. The knobs may also be arranged in a straight line, parallel to the axis of the segment, as shown by knobs 220 of segment 218 in FIG. 18. The knobbed designs may tend to especially increase turbulence externally. They may also tend to reduce the likelihood of thrombosis.

Figure 19:
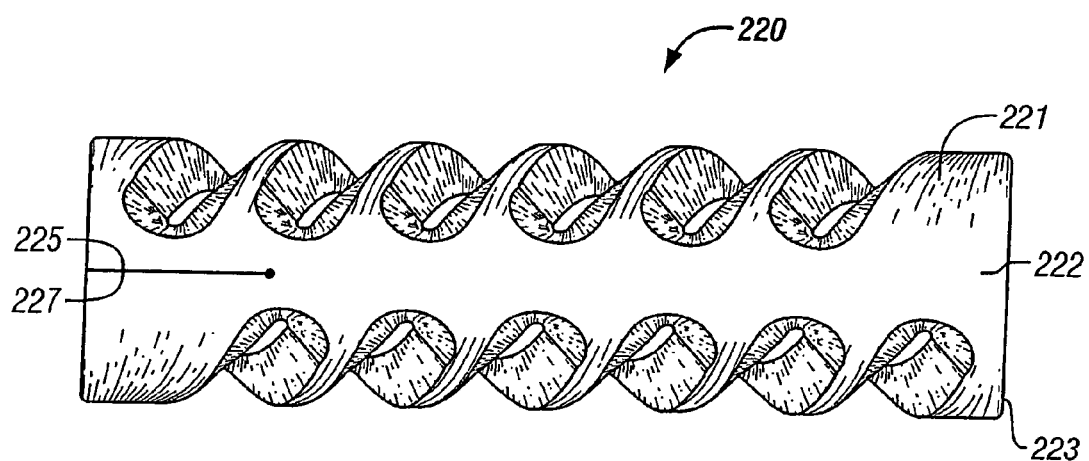

FIGS. 19 and 20 show two views, a top and side view, respectively, of a helical segment 220 that is especially capable of being molded by vapor deposition techniques or by inverse hydroforming or by stretchable injection molding (2 mold halves). In this embodiment, the segment 220 has a substantially cylindrical shape with helical features thereon, and the substantially cylindrical shape has a first half-cylinder 221 and a second half-cylinder 223. The first and second half-cylinders are joined at two sets of parting strips, of which only one, denoted 222, is shown. Each parting strip extends substantially parallel to an axis of the cylindrical shape. One set of helical ridges 224 or grooves 226, or both (as shown), are disposed on the first half-cylinder and another is disposed on the second half-cylinder.

As seen by the top of FIG. 20, the parting strip 222 is employed to serve as the location adjacent to which the two mold halves come together. In this way, all of the helical invaginations, formed by ridges 224 and grooves 226, may be formed without any undercut, thereby minimizing the difficulty of removing the segment from the mold. Of course, it will be seen that the "helical" grooves and ridges always subtend an angle of less than 180°, as none extends all the way around the segment. Such discontinuities may help to increase the overall amount of mixing or turbulence created. An additional advantage is that the distal 230 and proximal 228 ends may be more easily coupled to adjoining segments or joints (not shown).

A further embodiment is shown in FIG. 24. In this embodiment, a heat transfer segment 400 of a heat transfer element is shown. Heat transfer segment 400 has a "corkscrew" design, in which the helical ridge 402 and groove 404 forms a continuous ridge and groove from the proximal end 406 of the segment to the distal end 408.

Some designs for heat transfer elements without undercuts allow for their manufacture by injection molding processes. In general, the major drawback to injection molding is the requirement that the molded part not have any undercut features, i.e. any features which would prevent removal of the part from either half of the mold.

Figure 27:
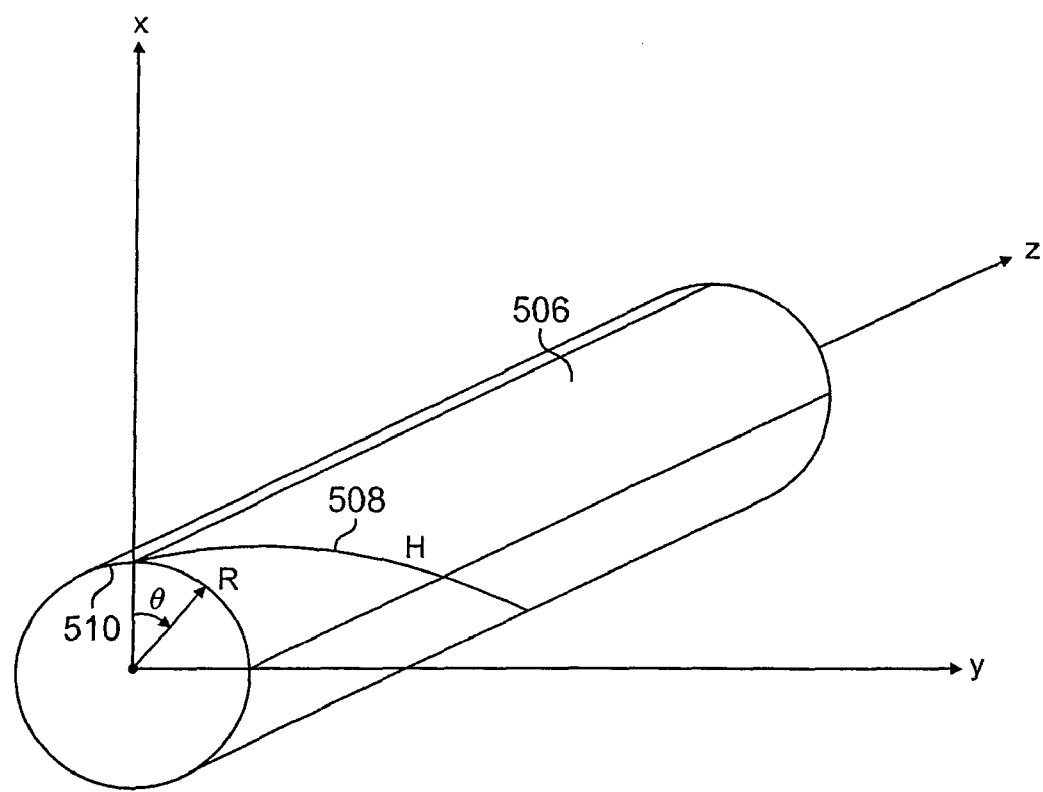
FIG. 27 shows a right circular cylinder in a global Cartesian reference frame demonstrating a helical path constrained to lie on the surface of the cylinder.
Figure 28:
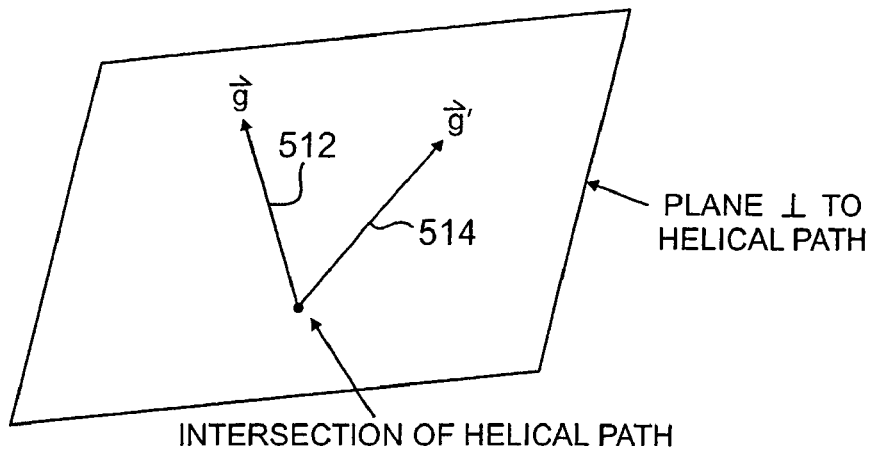
FIG. 28 shows vectors defining the helical grooves of a heat exchange element.
Figure 29:
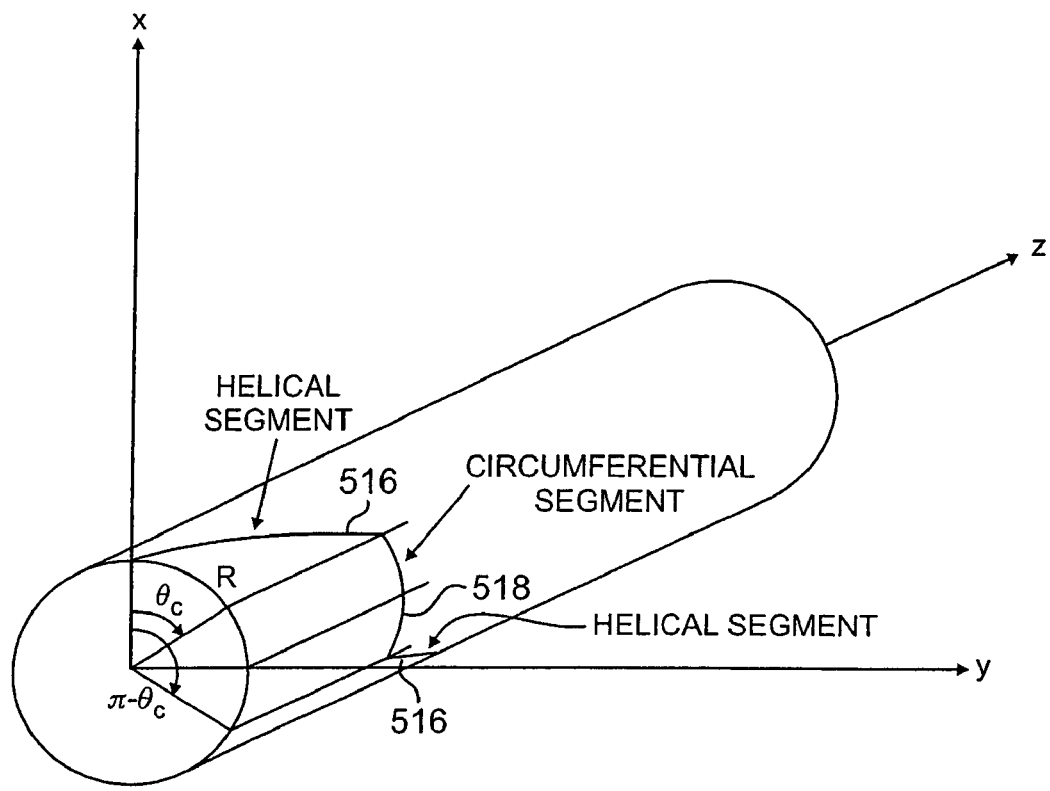
FIG. 29 shows a continuous path composed of helical segments joined by circumferential segments.

A right circular cylinder 506 is shown in the global Cartesian reference frame shown in FIG. 27, and a helical path 508 is constrained to lie in the surface of the cylinder and contains the point 510 (z=0, θ=0). The helical grooves of the heat exchange element can be constructed by sweeping the vectors $\vec{g}$ (512) and $\vec{g}'$ (514) (defined in FIG. 28), which satisfy the requirement $$(\vec{g} \times \vec{g}') \times \vec{t} = 0$$

along the helix 508. The vector $\vec{t}$ is the unit tangent vector to the helical path. At some point $\theta_c > 0$ for $\phi \neq 0$, a plane tangent to the groove wall, formed by the locus of vectors $\vec{g}$, will become normal to the global (y,z) plane. For $\theta > \theta_c$, the groove will exhibit undercut with respect to the global (y,z) plane. To eliminate the undercut, the groove is continued for $\theta > \Theta_c$ by sweeping the groove vectors $\vec{g}$ and $\vec{g}'$ along a path circumferential to the cylinder until $\theta = \pi - \theta_c$ at which point the helical path is resumed. The resulting continuous path is composed of helical segments 516 joined by circumferential segments 518 as shown schematically in FIG. 29. Exploiting the symmetry of the cylinder, two such grooves defined by the resulting path may start and end symmetrically on either side of the global (y,z) plane without intersecting.

Determination of Extinction Angle, $\theta_c$

The global coordinates of a helix constrained to lie in the surface of a cylinder, as shown in FIG. 27, are given by $$x = R\cos\theta$$
$$y = R\sin\theta$$
$$z = \frac{P}{2\pi}\theta$$

where P is the linear pitch of the helix (the distance along the 'z' axis of the cylinder traversed by $0 \leq \theta \leq 2\pi$). The tangent, normal, and bi-normal vectors at a point on the helix are given by $$\vec{t} = \left(-R\sin\theta, R\cos\theta, \frac{P}{2\pi}\right)$$
$$\vec{n} = (R\cos\theta, R\sin\theta, 0)$$
$$\vec{b} = \left(\frac{P}{2\pi}R\sin\theta, -\frac{P}{2\pi}R\cos\theta, R^2\right)$$

Figure 30:
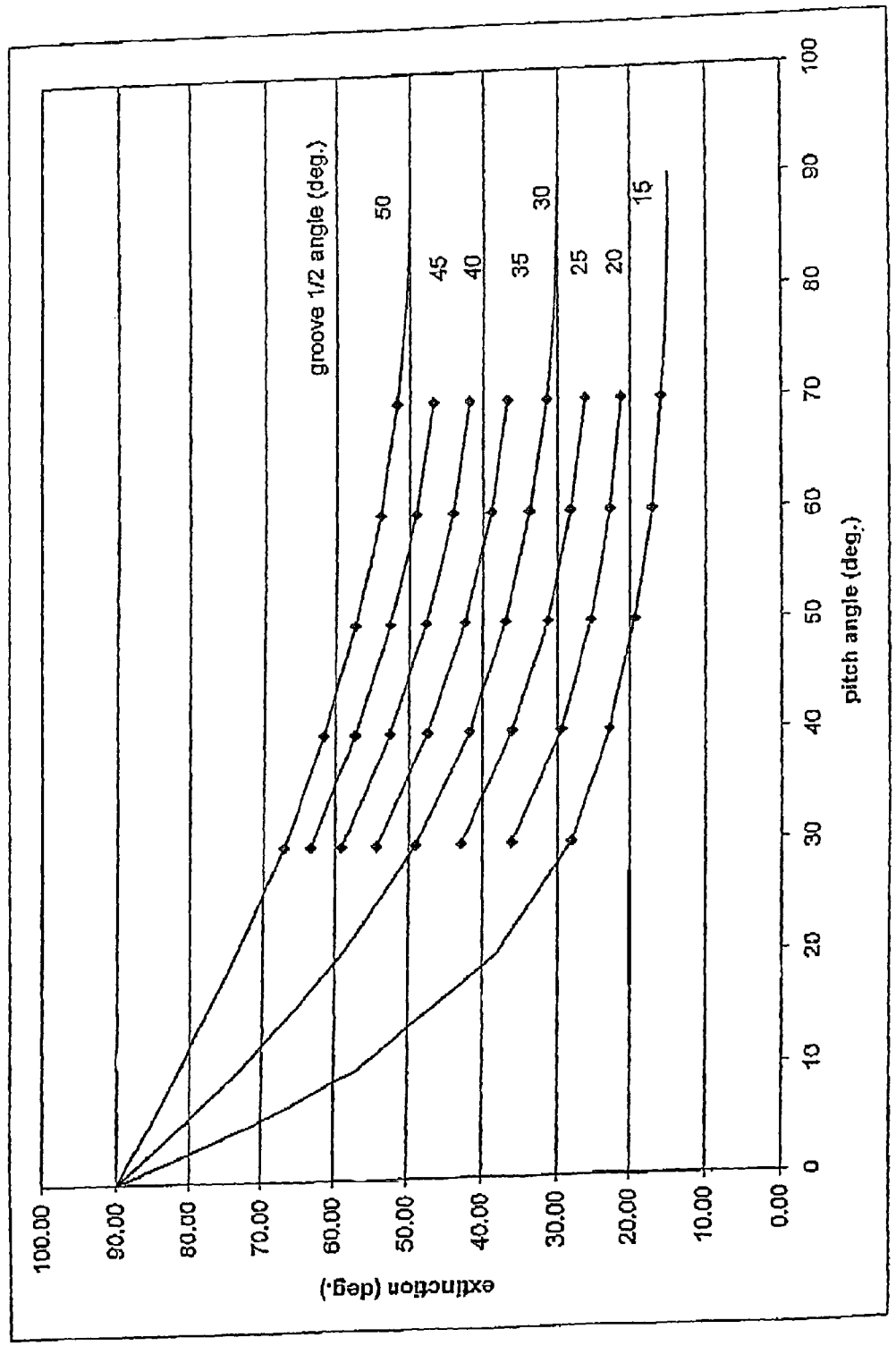
FIG. 30 shows the variation of extinction angle with helical pitch for a specified groove half-angle.

It can be assumed that these vectors have been normalized and therefore comprise a unit-orthonormal basis at any point on the helix. In the plane of the groove, the groove vector $\vec{g}$ can be constructed from components along the normal and bi-normal directions such that $$\vec{g} = \xi\vec{n} + \eta\vec{b}$$

where $\xi$ and $\eta$ are direction cosines of the vector $\vec{g}$ with respect to the normal and bi-normal directions. At $\theta_c$, a vector perpendicular to the groove wall will lie in the global (y,z) plane. Analytically, this becomes $$(\vec{g} \times \vec{t}) \cdot \hat{i} = 0$$

where $\hat{i}$ is the unit vector normal to the global (y,z) plane. $\theta_c$ is then the position along the helix at which the dot product is satisfied. The solution to that equation is presented graphically in FIG. 30. For a given helical pitch P and groove half-angle $\phi$, where $$\phi = \cos^{-1}(\vec{g} \cdot \hat{n}) = \cos^{-1}(\vec{g}' \cdot \hat{n}) \qquad \text{eq. 6}$$

and $\hat{n}$ is the unit vector in the helix normal direction, the above equation is evaluated in the interval $0 \leq \theta \leq \pi$ and $\theta_c$ is identified as the angle $\theta$ for which the triple product vanishes. The variation of extinction angle with helical pitch for a specified groove half-angle is shown in FIG. 30.

It may further be seen that by expressing the coordinates in dimensionless form that $\theta_c$ is independent of the cylinder radius.

Figure 31:
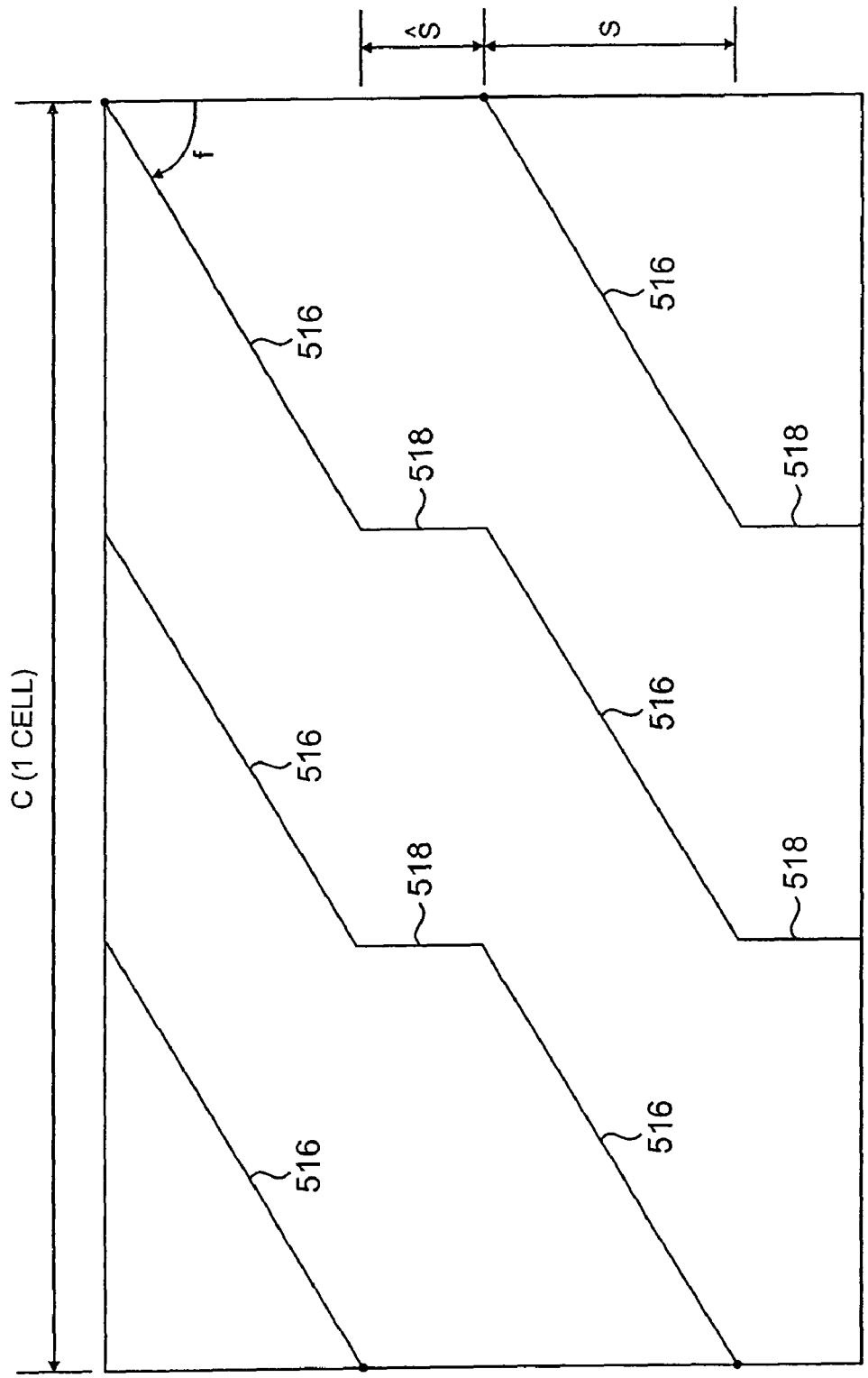
FIG. 31 shows a two-dimensional representation of helical segments joined by circumferential segments.
Figure 32:
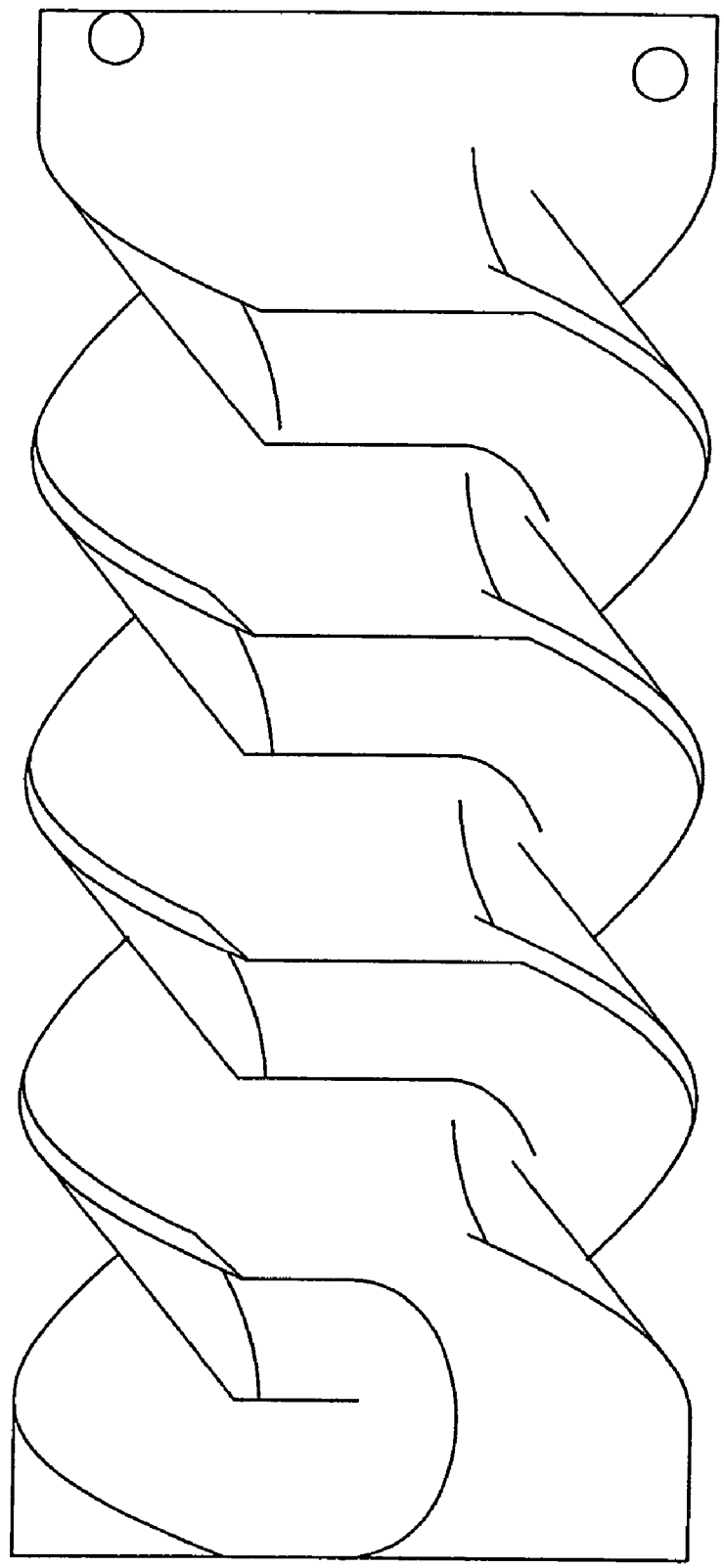
FIG. 32 shows a side view of a heat transfer element design with helical grooves connected by circumferential elements.
Figure 33:
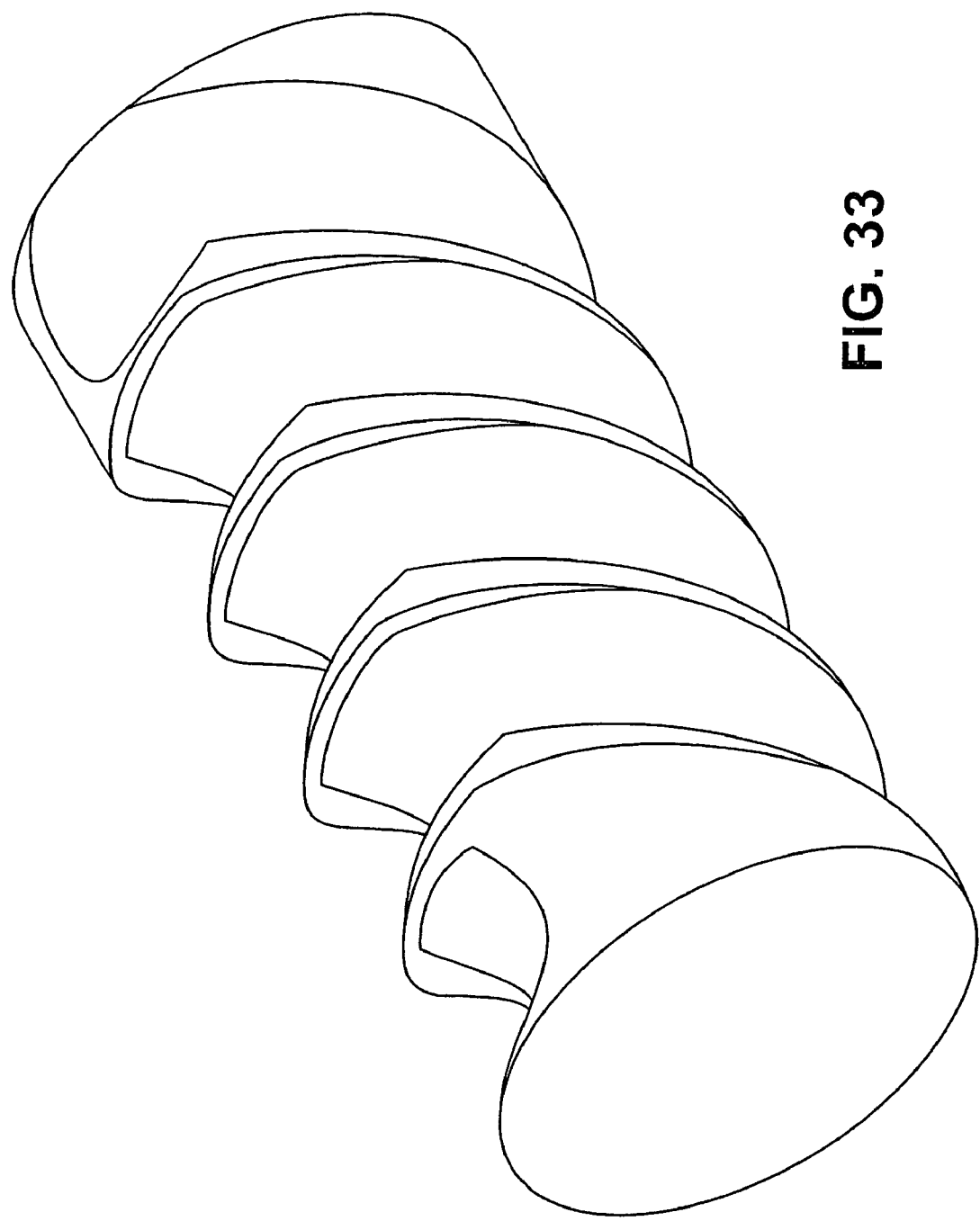
FIG. 33 shows a perspective view of a heat transfer element design with helical grooves connected by circumferential elements.

FIG. 31 shows a two-dimensional depiction of the helical segments 516 connected by circumferential segments 518, and FIGS. 32 and 33 show side and perspective views, respectively, of the same.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

The invention claimed is:

1. A method of making a heat transfer device, comprising:

Providing a mold in a deposition apparatus, the mold having an inside shape such that a flexible continuous substantially conductive layer may be deposited in the mold and shaped, configured, and arranged to have at least two helical grooves formed on a heat transfer segment, the two helical grooves being joined by a circumferential segment.

2. The method of claim 1, wherein the providing further comprises providing a mold that is shaped, configured, and arranged to form a layer that lacks undercuts.

3. The method of claim 1, wherein the inside shape forms at least two heat transfer segments, the helical grooves on one of the heat transfer segments having opposite helicity from the helical grooves on another of said heat transfer segments.

4. A product formed by the process of claim 3.

* * * * *